US007074598B2

(12) United States Patent
Cockerill, III et al.

(10) Patent No.: US 7,074,598 B2
(45) Date of Patent: Jul. 11, 2006

(54) DETECTION OF VANCOMYCIN-RESISTANT ENTEROCOCCUS SPP.

(75) Inventors: Franklin R. Cockerill, III, Rochester, MN (US); Lynne M. Sloan, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 470 days.

(21) Appl. No.: 10/254,260

(22) Filed: Sep. 25, 2002

(65) Prior Publication Data

US 2004/0058336 A1   Mar. 25, 2004

(51) Int. Cl.
C12P 19/34 (2006.01)
(52) U.S. Cl. .................. 435/91.2; 435/91.1; 435/6
(58) Field of Classification Search .............. 435/6, 435/91.1, 91.2; 536/23.1, 24.3, 24.32, 24.33, 536/25.32
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,800,159 | A | 1/1989 | Mullis et al. |
| 4,965,188 | A | 10/1990 | Mullis et al. |
| 4,996,143 | A | 2/1991 | Heller et al. |
| 5,035,996 | A | 7/1991 | Hartley |
| 5,565,322 | A | 10/1996 | Heller |
| 5,683,896 | A | 11/1997 | Hartley et al. |
| 5,702,895 | A | 12/1997 | Matsunaga et al. |
| 5,837,452 | A | 11/1998 | Clark et al. |
| 5,849,489 | A | 12/1998 | Heller |
| 5,945,313 | A | 8/1999 | Hartley et al. |
| 6,001,564 | A | 12/1999 | Bergeron et al. |
| 6,162,603 | A | 12/2000 | Heller |
| 6,593,093 | B1 | 7/2003 | Uhl et al. |

FOREIGN PATENT DOCUMENTS

| EP | 269 764 | 6/1988 |
| EP | 0 338 591 | 10/1989 |
| EP | 0 526 876 | 2/1993 |
| EP | 1 045 033 | 10/2000 |
| EP | 1 160 333 | 12/2001 |
| WO | WO 97/46707 | 12/1997 |
| WO | WO 97/46712 | 12/1997 |
| WO | WO 97/46714 | 12/1997 |
| WO | WO 98/48046 | 10/1998 |
| WO | WO 99/19466 | 4/1999 |
| WO | WO 99/45155 | 9/1999 |
| WO | WO 00/37646 | 6/2000 |
| WO | WO 00/70096 | 11/2000 |
| WO | WO 01/12803 | 2/2001 |
| WO | WO 01/23604 | 4/2001 |
| WO | WO 02/18660 | 3/2002 |
| WO | WO 02/34771 | 5/2002 |
| WO | WO 02/61390 | 8/2002 |
| WO | WO 02/92818 | 11/2002 |
| WO | WO 03/25216 | 3/2003 |
| WO | WO 03/068918 | 8/2003 |
| WO | WO 03/93306 | 11/2003 |

OTHER PUBLICATIONS

Pitt et al . Molecular bacteriology: a diagnostic tool for the millennium. Journal of clinical pathology, vol. 53, pp. 71-75, 2000.*
GenBank Accession No. AF310954.
GenBank Accession No. AY035705.
GenBank Accession No. M97297.
GenBank Accession No. U72704.
GenBank Accession No. U94528.
GenBank Accession No. X56895.
GenBank Accession No. 270527.
Patel et al., "Multiplex PCR Detection of vanA, vanB, vanC-1, and vanC-2/3 Genes in Enterococci," *Journal of Clinical Microbiology*, 1997, 35:703-707.
D'Agata et al., "High Rate of False-Negative Results of the Rectal Swab Culture Method in Detection of Gastrointestinal Colonization with Vancomycin-Resistant Enterococci," *Clinical Infectious Diseases*, 2002, 34:167-72.
Sloan et al., "Evaluation of a Combined LightCycler Assay for the Detection of vanA, vanB, and vanB-2/3 Genes in Enterococci," *Abstracts of the 102nd General Meeting of the American Society for Microbiology*, Salt Lake City, Utah, May 19-23, 2002, C-242.
Bassler et al., "Use of a Fluorogenic Probe in a PCR-Based Assay for the Detection of *Listeria monocytogenes*," *Applied and Environmental Microbiology*, 1995, 61(10):3724-3728.
Espy et al., "Diagnosis of Herpes Simplex Virus Infections in the Clinical Laboratory by LightCycler PCR," *J. Clin. Microbiol.*, 2000, 38(2):795-799.
Brink et al., "Nucleic Acid Sequence-Based Amplification, A New Method for Analysis of Spliced and Unspliced Epstein-Barr Virus Latent Transcripts, and Its Comparison with Reverse Transcriptase PCR," *J. Clin. Microbiol.*, 1998, 36(11):3164-3169.
Caplin et al., "LightCycler™ hybridization probes; The most direct way to monitor PCR amplification for quantification and mutation detection," *Biochemica*, 1999, 1:5-8.

(Continued)

*Primary Examiner*—Kenneth R. Horlick
*Assistant Examiner*—Cynthia Wilder
(74) *Attorney, Agent, or Firm*—Fish & Richardson P.C., P.A.

(57) ABSTRACT

The invention provides methods to detect vancomycin-resistant *enterococci* in biological samples using real-time PCR. Primers and probes for the detection of vancomycin-resistant *enterococci* are provided by the invention. Articles of manufacture containing such primers and probes for detecting vancomycin-resistant *enterococci* are further provided by the invention.

70 Claims, 6 Drawing Sheets

OTHER PUBLICATIONS

Espy et al., "Quantification of Epstein-Barr Virus (EBV) viral Load in Transplant Patients by LightCycler PCR," *Abstracts of the General Meeting of the American Society for Microbiology*, 101st General Meeting, May 20-24, 2001, 101:182, Abstract No. C-148.

Espy et al., "Diagnosis of Varicella-Zoster Virus Infections in the Clinical Laboratory by LightCycler PCR," *J. Clin. Microbiol.*, 2000, 38(9):3187-3189.

Espy et al., "Diagnosis of Herpes Simplex Virus Infections in the Clinical Laboratory by LightCycler PCR," *J. Clin. Microbiol.*, 2000, 38(2)795-799.

Espy et al., "Detection of Smallpox Virus DNA by LightCycler PCR," *J. Clin. Microbiol.*, 2002, 40(6):1985-1988.

Sample et al., "Two Related Epstein-Barr Virus Membrane Proteins are Encoded by Separate Genes," *J. Virol.*, 1989, 63(2):933-937.

Smith, "Application of Lightcycler Real Time PCR in Clinical Virology," *Clin. Chem. Lab. Med.*, 2001, Special Supplement, 39:S60, Abstract No. ISW14-2.

Telenti et al., "Detection of Epstein-Barr Virus by Polymerase Chain Reaction," *J. Clin. Microbiol.*, 1990, 28(10):2187-2190.

Al-Robaiy et al., "Rapid Competitive PCR Using Melting Curve Analysis for DNA Quantification," *BioTechniques*, 2001, 31:1382-1388.

Bélanger et al., "Rapid Detection of Shiga Toxin-Producing Bacteria in Feces by Multriplex PCR with Molecular Beacons on the Smart Cycler," *J. Clin. Microbiol.*, 2002, 40:1436-1440.

Bellin et al., "Rapid Detection of Enterohemorrhagic *Escherichia coli* by Real-Time PCR with Fluorescent Hybridization Probes," *J. Clin. Microbiol.*, 2001, 39:370-374.

Chen et al., An Automated Fluorescent PCR Method for Detection of Shiga Toxin-Producing *Escherichia coli* in Foods,: *Appl. Environ. Microbiol.*, 1998, 64:4210-4216.

Didenko, "DNA Probes Using Fluorescence Resonance Energy Transfer (FRET): Designs and Applications," *BioTechniques*, 2001, 31:1106-1121.

Ramotar et al., "Direct Detection of Verotoxin-Producing *Escherichia coli* in Stool Samples by PCR," *J. Clin. Microbiol.*, 1995, 33:519-524.

Livak et al., "Oligonucleotides with Fluorescent Dyes at Opposite Ends Provide A Quenched Probe System Useful for Detecting PCR Product and Nucleic Acid Hybridization," *Genome Research*, 1995, 4:357-362.

Arthur et al., "*Enterococcus faecium* transposon Tn1546 transposase, resolvase, vanR, vanS, vanH, vanA, vanX, vanY and teicoplanin resistance protein (vanZ) genes, complete cds," 1993, database accession No. M97297.

Grisold et al., "Detection of Methicillin-Resistant *Staphylococcus aureus* and Simultaneous Confirmation by Automated Nucleic Acid Extraction and Real-Time PCR," *J. Clin. Microbiol.*, 2002, 40:2392-2397.

Huletsky et al., "Rapid Detection of Vancomycin-Resistant Enterococci Directly from Rectal Swabs by Real-Time PCR Using the Smart Cycler," *Abstracts of the Interscience Conference on Antimicrobiol Agents and Chemotherapy*, Chicago, Illinois, Sep. 22-25, 2001, 41:409 (Abstract K-1195).

Ito et al., "*Staphylococcus aureus* DNA, type-I staphylococcal cassette chromosome mec," 1999, database accession No. AB033763.

"LightCycler-FastStart DNA Master Hybridization Probes," 1999 Roche Diagnostics GmbH Technical Manual, retrieved from the internet on Feb. 6, 2004: http://www.roche-applied-science.com.

Palladino et al., "Real-time PCR for the rapid detection of vanA and vanB genes," *Diagnostic Microbiology and Infectious Disease*, 2003, 45:81-84.

Palladino et al., "Rapid Detection of vanA and vanB Genes Directly from Clinical Specimens and Enrichment Broths by Real-Time Multiplex PCR Assay," *J. Clin. Microbiol.*, 2003, 41:2483-2486.

Patel et al., "*Enterococcus faecalis* vancomycin resistance protein vanB gene, partial cds," 1997, database accession No. U72704.

Patel et al., "*Enterococcus faecium* vancomycin resistance protein B (vanB) gene, partial cds," 1997, database accession No. U94528.

Petrich et al., "Direct detection of vanA and vanB genes in clinical specimens for rapid identification of vancomycin resistant enterococci (VRE) using multiplex PCR," *Molecular and Cellular Probes*, 1999, 13:275-281.

Reischl et al., "Rapid Identification of Methicillin-Resistant *Staphylococcus aureus* and Simultaneous Species Confirmation Using Real-Time Fluorescence PCR," *J. Clin. Microbiol.*, 2000, 38:2429-2433.

Sloan et al., "Evaluation of Combined LightCycler Assay for the Detection of vanA, vanB, and vanB-2/3 Genes in Enterococci," *Abstracts of the General Meeting of the American Society for Microbiology*, 2002, 102:143 (Abstract C-242).

Ryncarz et al., "Development of High-Throughput Quantitative Assay for Detecting Herpes Simplex Virus DNA in Clinical Samples," *J. Clin. Microbiol.*, 1999, 37:1941-1947.

Holland et al., "PCR Detection of *Escherichia coli* O157:H7 Directly from Stools: Evaluation of Commercial Extraction Methods for Purifying Fecal DNA," *J. Clin. Microbiol.*, 2000, 38:4108-4113.

Machiels et al., "New Protocol for DNA Extraction of Stool," *BioTechniques*, 2000, 28:286-290.

McOrist et al., "A comparison of five methods for extraction of bacterial DNA from human faecal samples," *J. Microbiological Methods*, 2002, 50:131-39.

Van der Hoek et al., "Isolation of Human Immunodeficiency Virus Type 1 (HIV-1) RNA from Feces by a Simple Method and Difference between HIV-1 Subpopulations in Feces and Serum," *J. Clin. Microbiol.*, 1995, 33:581-588.

Bergeron et al., "Rapid Detection of Group B Streptococci in Pregnant Women at Delivery." *New England J. Med.*, 2000, 343(3):175-179.

Ke et al., "Development of conventional and real-time PCR assays for the rapid detection of group B streptococci," *Clin. Chem.*, 2000, 46(3):324-331.

\* cited by examiner

| | | |
|---|---|---|
| >X56895 | #1 | ---------- ---------- ---------- ---------- ---------- |
| >M97297 | #1 | ---------- ---------- ---------- ---------- ---------- |
| | #1 | .......... .......... .......... .......... .......... GATATCGTTA CGCTTCATGT GCCGCTCAAT ACGGATACGC ACTATATTAT |
| >X56895 | #51 | ---------- ---------- ---------- ---------- ---------- |
| >M97297 | #51 | ---------- ---------- ---------- ---------- ---------- |
| | #51 | .......... .......... .......... .......... .......... CAGCCACGAA CAAATACAGA GAATGAAGCA AGGAGCATTT CTTATCAATA |
| >X56895 | #101 | ---------- ---------- ---------- ---------- ---------- |
| >M97297 | #101 | ---------- ---------- ---------- ---------- ---------- |
| | #101 | .......... .......... .......... .......... .......... CTGGGCGCGG TCCACTTGTA GATACCTATG AGTTGGTTAA AGCATTAGAA |
| >X56895 | #151 | ---------- ---------- ---------- ---------- ---------- |
| >M97297 | #151 | ---------- ---------- ---------- ---------- ---------- |
| | #151 | .......... .......... .......... .......... .......... AACGGGAAAC TGGGCGGTGC CGCATTGGAT GTATTGGAAG GAGAGGAAGA |
| >X56895 | #201 | ---------- ---------- ---------- ---------- ---------- |
| >M97297 | #201 | ---------- ---------- ---------- ---------- ---------- |
| | #201 | .......... .......... .......... .......... .......... GTTTTTCTAC TCTGATTGCA CCCAAAAACC AATTGATAAT CAATTTTTAC |
| >X56895 | #251 | ---------- ---------- ---------- ---------- ---------- |
| >M97297 | #251 | ---------- ---------- ---------- ---------- ---------- |
| | #251 | .......... .......... .......... .......... .......... TTAAACTTCA AGAATGCCT AACGTGATAA TCACACCGCA TACGGCCTAT |
| >X56895 | #301 | ---------- ---------- ---------- ---------- ---------- |
| >M97297 | #301 | ---------- ---------- ---------- ---------- ---------- |
| | #301 | .......... .......... .......... .......... .......... TATACCGAGC AAGCGTTGCG TGATACCGTT GAAAAAACCA TTAAAAACTG |
| >Van A | >#1> | ---- ---------- ---------- |
| >X56895 | #351 | ---------- ---------- ---------- ---------- ---------- |
| >M97297 | #351 | ---------- ---------- ---------- ---------- ---------- |
| | #351 | .......... .......... .......... .......... .......... TTTGGATTTT GAAAGGAGAC AGGAGCATGA ATAGAATAAA AGTTGCAATA |
| >Van A | #25 | ---------- ---------- ---------- ---------- ---------- |
| >X56895 | #401 | ---------- ---------- ---------- ---------- ---------- |
| >M97297 | #401 | ---------- ---------- ---------- ---------- ---------- |
| | #401 | .......... .......... .......... .......... .......... CTGTTTGGGG GTTGCTCAGA GGAGCATGAC GTATCGGTAA AATCTGCAAT |
| >Van A | #75 | ---------- ---------- ---------- ---------- ---------- |
| >X56895 | #451 | ---------- ---------- ---------- ---------- ---------- |
| >M97297 | #451 | ---------- ---------- ---------- ---------- ---------- |
| | #451 | .......... .......... .......... .......... .......... AGAGATAGCC GCTAACATTA ATAAGAAAA ATACGAGCCG TTATACATTG |
| >Van A | #125 | ---------- ---------- ---------- ---------- ---------- |
| >X56895 | #501 | ---------- ---------- ---------- ---------- ---------- |
| >M97297 | #501 | ---------- ---------- ---------- ---------- ---------- |
| | #501 | .......... .......... .......... .......... .......... GAATTACGAA ATCTGGTGTA TGGAAAATGT GCGAAAAACC TTGCGCGGAA |
| >Van A | #175 | ---------- ---------- ---------- ---------- ---------- |
| >X56895 | #551 | ---------- ---------- ---------- ---------- ---------- |
| >M97297 | #551 | ---------- ---------- ---------- ---------- ---------- |
| | #551 | .......... .......... .......... .......... .......... TGGGAAAACG ACAATTGCTA TTCAGCTGTA CTCTCGCCGG ATAAAAAAAT |
| >Van A | #225 | ---------- ---------- ---------- ---------- ---------- |
| >X56895 | #601 | ---------- ---------- ---------- ---------- ---------- |
| >M97297 | #601 | ---------- ---------- ---------- ---------- ---------- |
| | | .......... .......... .......... .......... .......... |

Figure 1-1

|         |       |                                                                |
|---------|-------|----------------------------------------------------------------|
|         | #601  | GCACGGATTA CTTGTTAAAA AGAACCATGA ATATGAAATC AACCATGTTG         |
| >Van A  | #275  | ---------- ---------- ---------- ---------- ----------         |
| >X56895 | #651  | ---------- ---------- ---------- ---------- ----------         |
| >M97297 | #651  | ---------- ---------- ---------- ---------- ----------         |
|         | #651  | ATGTAGCATT TTCAGCTTTG CATGGCAAGT CAGGTGAAGA TGGATCCATA         |
| >Van A  | #325  | ---------- ---------- ---------- ---------- ----------         |
| >X56895 | #701  | ---------- ---------- ---------- ---------- ----------         |
| >M97297 | #701  | ---------- ---------- ---------- ---------- ----------         |
|         | #701  | CAAGGTCTGT TTGAATTGTC CGGTATCCCT TTTGTAGGCT GCGATATTCA         |
| >Van A  | #375  | ---------- ---------- ---------- ---------- ----------         |
| >X56895 | #751  | ---------- ---------- ---------- ---------- ----------         |
| >M97297 | #751  | ---------- ---------- ---------- ---------- ----------         |
|         | #751  | AAGCTCAGCA ATTTGTATGG ACAAATCGTT GACATACATC GTTGCGAAAA         |
| >Van A  | #425  | ---------- ---------- ---------- ---------- ----------         |
| >X56895 | #801  | ---------- ---------- ---------- ---------- ----------         |
| >M97297 | #801  | ---------- ---------- ---------- ---------- ----------         |
|         | #801  | ATGCTGGGAT AGCTACTCCC GCCTTTTGGG TTATTAATAA AGATGATAGG         |
| >Van A  | #475  | ---------- ---------- ---------- ---------- ----------         |
| >X56895 | #851  | ---------- ---------- ---------- ---------- ----------         |
| >M97297 | #851  | ---------- ---------- ---------- ---------- ----------         |
|         | #851  | CCGGTGGCAG CTACGTTTAC CTATCCTGTT TTTGTTAAGC CGGCGCGTTC         |
| >Van A  | #525  | ---------- ---------- ---------- ---------- ----------         |
| >X56895 | #901  | ---------- ---------- ---------- ---------- ----------         |
| >M97297 | #901  | ---------- ---------- ---------- ---------- ----------         |
|         | #901  | AGGCTCATCC TTCGGTGTGA AAAAAGTCAA TAGCGCGGAC GAATTGGACT         |
| >Van A  | #575  | ---------- ---------- ---------- ---------- ----------         |
| >X56895 | #951  | ---------- ---------- ---------- ---------- ----------         |
| >M97297 | #951  | ---------- ---------- ---------- ---------- ----------         |
|         | #951  | ACGCAATTGA ATCGGCAAGA CAATATGACA GCAAAATCTT AATTGAGCAG         |
| >Van A  | #625  | ---------- ---------- ---------- ---------- ----------         |
| >X56895 | #1001 | ---------- ---------- ---------- ---------- ----------         |
| >M97297 | #1001 | ---------- ---------- ---------- ---------- ----------         |
|         | #1001 | GCTGTTTCGG GCTGTGAGGT CGGTTGTGCG GTATTGGGAA ACAGTGCCGC         |
| >Van A  | #675  | ---------- ---------- ---------- ---------- ----------         |
| >X56895 | #1051 | ---------- ---------- ---------- ---------- ----------         |
| >M97297 | #1051 | ---------- ---------- ---------- ---------- ----------         |
|         | #1051 | GTTAGTTGTT GGCGAGGTGG ACCAAATCAG GCTGCAGTAC GGAATCTTTC         |
| >Van A  | #725  | ---------- ---------- ---------- ---------- ----------         |
| >X56895 | #1101 | ---------- ---------- ---------- ---------- ----------         |
| >M97297 | #1101 | ---------- ---------- ---------- ---------- ----------         |
|         | #1101 | GTATTCATCA GGAAGTCGAG CCGGAAAAAG CTCTGAAAA CGCAGTTATA          |
| >Van A  | #775  | ---------- ---------- ---------- ---------- ----------         |
| >X56895 | #1151 | ---------- ---------- ---------- ---------- ----------         |
| >M97297 | #1151 | ---------- ---------- ---------- ---------- ----------         |
|         | #1151 | ACCGTTCCCG CAGACCTTTC AGCAGAGGAG CGAGGACGGA TACAGGAAAC         |

Figure 1-2

| | | |
|---|---|---|
| >Van A | #825 | ---------- ---------- ---------- ---------- ---------- |
| >X56895 | #1201 | ---------- ---------- ---------- ---------- ---------- |
| >M97297 | #1201 | ---------- ---------- ---------- ---------- ---------- |
| | #1201 | .......... .......... .......... .......... .......... <br> GGCAAAAAAA ATATATAAAG CGCTCGGCTG TAGAGGTCTA GCCCGTGTGG |
| >Van A | #875 | ---------- ---------- ---------- ---------- ---------- |
| >X56895 | #1251 | ---------- ---------- ---------- ---------- ---------- |
| >M97297 | #1251 | ---------- ---------- ---------- ---------- ---------- |
| | #1251 | .......... .......... .......... .......... .......... <br> ATATGTTTTT ACAAGATAAC GGCCGCATTG TACTGAACGA AGTCAATACT |
| >Van A | #925 | ---------- ---------- ---------- ---------- ---------- |
| >X56895 | #1301 | ---------- ---------- ---------- ---------- ---------- |
| >M97297 | #1301 | ---------- ---------- ---------- ---------- ---------- |
| | #1301 | .......... .......... .......... .......... .......... <br> CTGCCCGGTT TCACGTCATA CAGTCGTTAT CCCCGTATGA TGGCCGCTGC |
| >Van A | #975 | ---------- ---------- ---------- ---------- ---------- |
| >X56895 | #1351 | ---------- ---------- ---------- ---------- ---------- |
| >M97297 | #1351 | ---------- ---------- ---------- ---------- ---------- |
| | #1351 | .......... .......... .......... .......... .......... <br> AGGTATTGCA CTTCCCGAAC TGATTGACCG CTTGATCGTA TTAGCGTTAA |
| >Van A | #1025 | --------NN (SEQ ID NO:9) |
| >X56895 | #1401 | ---------- ---------- ---------- ---------- ---------- |
| >M97297 | #1401 | ---------- ---------- ---------- ---------- ---------- |
| | #1401 | .......... .......... .......... .......... .......... <br> AGGGGTGATA AGCATGGAAA TAGGATTTAC TTTTTTAGAT GAAATAGTAC <br>               ++ |
| >X56895 | #1451 | ---------- ---------- ---------- ---------- ---------- |
| >M97297 | #1451 | ---------- ---------- ---------- ---------- ---------- |
| | #1451 | .......... .......... .......... .......... .......... <br> ACGGTGTTCG TTGGGACGCT AAATATGCCA CTTGGGATAA TTTCACCGGA |
| >X56895 | #1501 | ---------- ---------- ---------- ---------- ---------- |
| >M97297 | #1501 | ---------- ---------- ---------- ---------- ---------- |
| | #1501 | .......... .......... .......... .......... .......... <br> AAACCGGTTG ACGGTTATGA AGTAAATCGC ATTGTAGGGA CATACGAGTT |
| >X56895 | #1551 | ---------- ---------- ---------- ---------- ---------- |
| >M97297 | #1551 | ---------- ---------- ---------- ---------- ---------- |
| | #1551 | .......... .......... .......... .......... .......... <br> GGCTGAATCG CTTTTGAAGG CAAAAGAACT GGCTGCTACC CAAGGGTACG |
| >X56895 | #1601 | ---------- ---------- ---------- ---------- ---------- |
| >M97297 | #1601 | ---------- ---------- ---------- ---------- ---------- |
| | #1601 | .......... .......... .......... .......... .......... <br> GATTGCTTCT ATGGGACGGT TACCGTCCTA AGCGTGCTGT AAACTGTTTT |
| >X56895 | #1651 | ---------- ---------- ---------- ---------- ---------- |
| >M97297 | #1651 | ---------- ---------- ---------- ---------- ---------- |
| | #1651 | .......... .......... .......... .......... .......... <br> ATGCAATGGG CTGCACAGCC GGAAAATAAC CTGACAAAGG AAAGTTATTA |
| >X56895 | #1701 | ---------- ---------- ---------- ---------- ---------- |
| >M97297 | #1701 | ---------- ---------- ---------- ---------- ---------- |
| | #1701 | .......... .......... .......... .......... .......... <br> TCCCAATATT GACCGAACTG AGATGATTTC AAAAGGATAC GTGGCTTCAA |
| >X56895 | #1751 | ---------- --------- (SEQ ID NO:10) |
| >M97297 | #1751 | ---------- --------- (SEQ ID NO:11) |
| | #1751 | .......... ........ <br> AATCAAGCCA TAGCCGCG (SEQ ID NO:10) |

Figure 1-3

```
<gi|8100655:28.#1      ---------- ---------- ---------- ---------- ----------
>EFU94528      >#1>                                                         --
>EFU94529      >#1>                                                         --
>EFU94526      >#1>                                                         --
>EFU94530      >#1>                                                         --
>EFU94527      >#1>                                                         --
<ENEVANB       >#1>                                                         --
<EFU72704      >#1>                                                         --
<ENEVANB2A     >#1>                                                         --
                     .......... .......... .......... .......... ..........
               #1    ACCAGGCAGG GTATTGACCT CATTTAGAAC GATGCCGCCA TCCTCCTGCA

<gi|8100655:28.#51    ---------- ---------- ---------- ---------- ----------
>EFU94528      #3     ---------- ---------- ---------- ---------- ----------
>EFU94529      #3     ---------- ---------- ---------- ---------- ----------
>EFU94526      #3     ---------- ---------- ---------- ---------- ----------
>EFU94530      #3     ---------- ---------- ---------- ---------- ----------
>EFU94527      #3     ---------- ------A--- ---------- ---------- ----------
<ENEVANB       #3     ---------- ------A--- ---------- ---------- ----------
<EFU72704      #3     ---------- ---------- ---------- --------G- ----------
<ENEVANB2A     #3     ---------- ---------- ---------- ---------- ----------
                     .......... .......... .......... .......... ..........
               #51   AAAAAAGATC AACACGGGCA AGCCCTCTGC ATCCAAGCAC CCGATATACT
                                    *                     *

<gi|8100655:28.#101   ---------- ---------- ---------- ---------- ----------
>EFU94528      #53    ---------- ---------- ---------- ---------- ----------
>EFU94529      #53    ---------- ---------- ---------- ---------- ----------
>EFU94526      #53    ---------- ---------- ---------- ---------- ----------
>EFU94530      #53    ---------- ---------- ---------- ---------- ----------
>EFU94527      #53    ---------- ----T----- ---------- ---------- ----------
<ENEVANB       #53    ---------- ----T----- ---------- ---------- ----------
<EFU72704      #53    ---------- ---------- ---------- ---C----T- -G--------
<ENEVANB2A     #53    ---------- ---------- ---------- ---------- ----------
                     .......... .......... .......... .......... ..........
               #101  TTCTTTGCCG TTTCCTGCAC CCGATTCHT TCCTCGACCG GAATGTCTGC
                                       *              *    *    *

<gi|8100655:28.#151   ---------- ---------- ---------- ---------- ----------
>EFU94528      #103   ---------- ---------- ---------- ---------- ----------
>EFU94529      #103   ---------- ---------- ---------- ---------- ----------
>EFU94526      #103   ---------- ---------- ---------- ---------- ----------
>EFU94530      #103   ---------- ---------- ---------- ---------- ----------
>EFU94527      #103   T-----GA-- ---------- -C-------- ---------- ----------
<ENEVANB       #103   T-----GA-- ---------- -C-------- ---------- ----------
<EFU72704      #103   A-----G--- ---------- -C-----T-- ---------- ----------
<ENEVANB2A     #103   ---------- ---------- ---------- ---------- ----------
                     .......... .......... .......... .......... ..........
               #151  GGGAACTGTA ATCATCGCAT TTTCTGAGCC TTTTTCCGGC PCGTTTTCCT
                     *     **              *     *

<gi|8100655:28.#201   ---------- ---------- ---------- ---------- ----------
>EFU94528      #153   ---------- ---------- ---------- ---------- ----------
>EFU94529      #153   ---------- ---------- ---------- ---------- ----------
>EFU94526      #153   ---------- ---------- ---------- ---------- ----------
>EFU94530      #153   ---------- ---------- ---------- ---------- ----------
>EFU94527      #153   ---------- ---------- -------A-- ---------- ----------
<ENEVANB       #153   ---------- ---------- -------A-- ---------- ----------
<EFU72704      #153   ---------- ---------A ---------- ---------- ----------
<ENEVANB2A     #153   ---------- ---------- ---------- ---------- ----------
                     .......... .......... .......... .......... ..........
               #201  GATGGATGCG GAAGATACCG TGGCTCAGCC GGATTTGATC CACTTCGCCG
                                     *              *

<gi|8100655:28.#251   ---------- ---------- ---------- ---------- ----------
>EFU94528      #203   ---------- ---------- ---------- ---------- ----------
>EFU94529      #203   ---------- ---------- ---------- ---------- ----------
>EFU94526      #203   ---------- ---------- ---------- ---------- ----------
>EFU94530      #203   ---------- ---------- ---------- ---------- ----------
>EFU94527      #203   ---------- ---------- T--------- --G--G---- ----------
```

Figure 2-1

```
<ENEVANB       #203                 ---------- ---------- T--------- --G--G---- ----------
<EFU72704      #203                 ---------- ---------- ------A--- ----G----- ----------
<ENEVANB2A     #203                 ---------- ---------- ---------- ---------- ----------
                                    .......... .......... .......... .......... ..........
               #251                 ACAATCAAAT CATCCTCGTT CCCCATGACC GCACACCCGA CCTCACAGCC
                                                    *  *                 *  *
                                       Red640 Probe BB-R                W099/01571

<gi|8100655:28.#301                 ---------- ---------- ---------- ---------- ----------
>EFU94528      #253                 ---------- ---------- ---------- ---------- ----------
>EFU94529      #253                 ---------- ---------- ---------- ---------- ----------
>EFU94526      #253                 ---------- ---------- ---------- ---------- ----------
>EFU94530      #253                 ---------- ---------- ---------- ---------- ----------
>EFU94527      #253                 ---------- ---------- ---------- ---------- -----T----
<ENEVANB       #253                 ---------- ---------- ---------- ---------- -----T----
<EFU72704      #253                 ---------- ---------- ---------- ---------- ----------
<ENEVANB2A     #253                 ---------- ---------- ---------- ---------- ----------
                                    .......... .......... .......... .......... ..........
               #301                 CGAAATCGCT TGCTCAATTA AGATTTTTCC ATCATATTGT CCTGCCGCTT
                                                                                         *

<gi|8100655:28.#351                 ---------- ---------- ---------- ---------- ----------
>EFU94528      #303                 ---------- ---------- ---------- ---------- ----------
>EFU94529      #303                 ---------- ---------- ---------- ---------- ----------
>EFU94526      #303                 ---------- ---------- ---------- ---------- ----------
>EFU94530      #303                 ---------- ---------- ---------- ---------- ----------
>EFU94527      #303                 ---------- ---T------ -------T-- ---------- ----------
<ENEVANB       #303                 ---------- ---T------ -------T-- ---------- ----------
<EFU72704      #303                 ---------- ---------- ---------- ---------- --A-------
<ENEVANB2A     #303                 ---------- ---------- ---------- ---------- ----------
                                    .......... .......... .......... .......... ..........
               #351                 CTATCGCAGC GTTAAGTTCT TCCGTACCGT TTACTTTGGT TACGCCAAAG
                                             *                 *                *

<gi|8100655:28.#401                 ---------- ---------- ---------- ---------- ----------
>EFU94528      #353                 ---------- ---------- ---------- ---------- ----------
>EFU94529      #353                 ---------- ---------- ---------- ---------- ----------
>EFU94526      #353                 ---------- ---------- ---------- ---------- ----------
>EFU94530      #353                 ---------- ---------- ---------- ---------- ----------
>EFU94527      #353                 ---------- ---------- ---------- ---------- ------TC-T
<ENEVANB       #353                 ---------- ---------- ---------- ---------- ------TC-T
<EFU72704      #353                 ---------- ---------- ---------- ---------- ----------
<ENEVANB2A     #353                 ---------- ---------- ---------- ---------- ----------
                                    .......... .......... .......... .......... ..........
               #401                 GACGAACCTG ACCGTGCCGG CTTCACAAAG ACAGGGTAGG TAAGCGCACC
                                                                                 **  *

<gi|8100655:28.#451                 ---------- ---------- ---------- ---------- ----------
>EFU94528      #403                 ---------- ---------- -------A-- ---------- ----------
>EFU94529      #403                 ---------- ---------- -------A-- ---------- ----------
>EFU94526      #403                 ---------- ---------- ---------- ---------- ----------
>EFU94530      #403                 ---------- ---------- -------A-- ---------- ----------
>EFU94527      #403                 ---------T ---------- -T-------- ---------- --G-------
<ENEVANB       #403                 ---------T ---------- -T-------- ---------- --G-------
<EFU72704      #403                 --T------- ---------- ---------- ---------- ----------
<ENEVANB2A     #403                 ---------- ---------- ---------- ---------- ----------
                                    .......... .......... .......... .......... ..........
               #451                 CGCCTCCGGC TTGTCACCTT TATCAATCAT TGAAATTCG  GGAACGGCGA
                                       *    *               *  *                *

<gi|8100655:28.#501                 ---------- ---------- ---------- ---------- ----------
>EFU94528      #453                 ---------- ---------- ---------- ---------- ----------
>EFU94529      #453                 ---------- ---------- ---------- ---------- ----------
>EFU94526      #453                 ---------- ---------- ---------- ---------- ----------
>EFU94530      #453                 ---------- ---------- ---------- ---------- ----------
>EFU94527      #453                 ---------- ---------- ---------- ---------- ----------
<ENEVANB       #453                 ---------- ---------- ---------- ---------- ----------
<EFU72704      #453                 ---------- ---------- ---------- ---------- ----------
<ENEVANB2A     #453                 ---------- ---------- ---------- ---------- ----------
                                    .......... .......... .......... .......... ..........
               #501                 TGCCCGCATT TTTTGTAAGA ATGTAGGCCA GTGATTTGTC CATGCAAGCT
```

Figure 2-2

```
<gi|8100655:28.#551  ---------- -------G-- ---T------ ---------- ----------
>EFU94528     #503  ---------- ---------- ---------- ---------- -----A----
>EFU94529     #503  ---------- ---------- ---------- ---------- -----A----
>EFU94526     #503  ---------- ---------- ---------- ---------- -----A----
>EFU94530     #503  ---------- ---------- ---------- ---------- -----A----
>EFU94527     #503  ---------- -------G-- ---T------ ---------- ----------
<ENEVANB      #503  ---------- -------G-- ---T------ ---------- ----------
<EFU72704     #503  ---------- -------G-- ---------- -----G---- ----------
<ENEVANB2A    #503  ---------- ---------- ---------- ---------- ----------
                    .......... .......... .......... .......... ..........
              #551  GCGGAGCTTT GAATATCACA GCCCACATAG GGGATACCAG ACAATTCAAA
                                  *              *             *         *

<gi|8100655:28.#601  ---A------ ----------  ---------- ---------- ----------
>EFU94528     #553  ---C (SEQ ID NO:13)
>EFU94529     #553  ---C (SEQ ID NO:14)
>EFU94526     #553  ---C (SEQ ID NO:15)
>EFU94530     #553  ---C (SEQ ID NO:16)
>EFU94527     #553  ---A (SEQ ID NO:17)
<ENEVANB      #553  ---A (SEQ ID NO:18)
<EFU72704     #553  T-AA (SEQ ID NO:19)
<ENEVANB2A    #553  ---T (SEQ ID NO:20)
                    .......... .......... .......... .......... ..........
              #601  CAGMCCCTGT ATCGCACCAT CCTCCCCGCA TTTGCCATGC AAAACCGGGA
                    *  **

<gi|8100655:28.#651  ---------- ---------- ---------- ---------- ----------
                    .......... .......... .......... .......... ..........
              #651  AAGCCACATC AATACGCCGT GTTTCGTATT CGCTTTCTTT CATGACAAGC

<gi|8100655:28.#701  ---------- ---------- ---------- ---------- ----------
                    .......... .......... .......... .......... ..........
              #701  AGCCCATGCG TTTTCCTATC CGGGGAGAGT ATGGCGGGGA GACTGTCGGC

<gi|8100655:28.#751  ---------- ---------- ---------- ---------- ----------
                    .......... .......... .......... .......... ..........
              #751  TTCCCATTCC GTACATGGCT TCTTGCATAG CTTCCATACG CCGTTTTTTG

<gi|8100655:28.#801  ---------- ---------- ---------- ---------- ----------
                    .......... .......... .......... .......... ..........
              #801  TAATTCCGAT GTAGTGCGGA TCGAATTTTT CAGTATTAAT GTTCGCAGCA

<gi|8100655:28.#851  ---------- ---------- ---------- -- (SEQ ID NO:12)
                    .......... .......... .......... ..
              #851  ATTTCTATTG CGGATTTTAC CGACACATCA TG (SEQ ID NO:12)
```

Figure 2-3

SEQUENCE LISTING

```
<160> NUMBER OF SEQ ID NOS: 20

<210> SEQ ID NO 1
<211> LENGTH: 17
<212> TYPE: DNA
<213> ORGANISM: Artificial Sequence
<220> FEATURE:
<223> OTHER INFORMATION: Oligonucleotide

<400> SEQUENCE: 1
cgaggacgga tacagga                                                        17

<210> SEQ ID NO 2
<211> LENGTH: 19
<212> TYPE: DNA
<213> ORGANISM: Artificial Sequence
<220> FEATURE:
<223> OTHER INFORMATION: Oligonucleotide

<400> SEQUENCE: 2
cttatcaccc ctttaacgc                                                      19

<210> SEQ ID NO 3
<211> LENGTH: 29
<212> TYPE: DNA
<213> ORGANISM: Artificial Sequence
<220> FEATURE:
<223> OTHER INFORMATION: Oligonucleotide

<400> SEQUENCE: 3
caagataacg gccgcattgt actgaacga                                           29

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide

<400> SEQUENCE: 4
gtcaatactc tgcccggttt cac                                                 23
```

<210> SEQ ID NO 5
<211> LENGTH: 17
<212> TYPE: DNA
<213> ORGANISM: Artificial Sequence
<220> FEATURE:
<223> OTHER INFORMATION: Oligonucleotide

<400> SEQUENCE: 5
gaagataccg tggctca                                                17

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
gtacggaaga acttaacgct                                             20

<210> SEQ ID NO 7
<211> LENGTH: 18
<212> TYPE: DNA
<213> ORGANISM: Artificial Sequence
<220> FEATURE:
<223> OTHER INFORMATION: Oligonucleotide

<400> SEQUENCE: 7
gatccacttc gccgacaa                                               18

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
aaatcatcct cgtttcccat                                             20

<210> SEQ ID NO 9
<211> LENGTH: 1034
<212> TYPE: DNA
<213> ORGANISM: Enterococcus faecium
<220> FEATURE:
<221> NAME/KEY: variation
<222> LOCATION: 1033, 1034
<223> OTHER INFORMATION: n = a, t, c or g;
      vanA sequence

<400> SEQUENCE: 9
atgaatagaa taaaagttgc aatactgttt ggggggttgct cagaggagca tgacgtatcg    60
gtaaaatctg caatagagat agccgctaac attaataaag aaaaatacga gccgttatac   120
attggaatta cgaaatctgg tgtatggaaa atgtgcgaaa accttgcgc ggaatgggaa     180 aacgacaatt gctattcagc tgtactctcg ccggataaaa aaatgcacgg attacttgtt   240
aaaaagaacc atgaatatga atcaaccat gttgatgtag cattttcagc tttgcatggc    300
aagtcaggtg aagatggatc catacaaggt ctgtttgaat tgtccggtat ccttttttgta  360 ggctgcgata ttcaaagctc agcaatttgt atggacaaat cgttgacata catcgttgcg   420
aaaaatgctg ggatagctac tcccgccttt tgggttatta ataaagatga taggccggtg   480
gcagctacgt ttacctatcc tgttttttgtt aagccggcgc gttcaggctc atccttcggt  540
gtgaaaaaag tcaatagcgc ggacgaattg gactacgcaa ttgaatcggc aagacaatat   600

```
gacagcaaaa tcttaattga gcaggctgtt tcgggctgtg aggtcggttg tgcggtattg      660
ggaaacagtg ccgcgttagt tgttggcgag gtggaccaaa tcaggctgca gtacggaatc      720
tttcgtattc atcaggaagt cgagccgaaa aaggctctg aaaacgcagt tataaccgtt       780
cccgcagacc tttcagcaga ggagcgagga cggatacagg aaacggcaaa aaaaatatat      840
aaagcgctcg gctgtagagg tctagcccgt gtggatatgt ttttacaaga taacggccgc      900
attgtactga acgaagtcaa tactctgccc ggtttcacgt catacagtcg ttatccccgt      960
atgatggccg ctgcaggtat tgcacttccc gaactgattg accgcttgat cgtattagcg     1020
ttaaaggggt gann                                                       1034

<210> SEQ ID NO 10
<211> LENGTH: 1768
<212> TYPE: DNA
<213> ORGANISM: Enterococcus faecium
<220> FEATURE:
<223> OTHER INFORMATION: vanA sequence

<400> SEQUENCE: 10
gatatcgtta cgcttcatgt gccgctcaat acggatacgc actatattat cagccacgaa       60
caaatacaga gaatgaagca aggagcattt cttatcaata ctgggcgcgg tccacttgta      120
gatacctatg agttggttaa agcattagaa acgggaaac tgggcggtgc cgcattggat       180
gtattggaag gagaggaaga gttttttctac tctgattgca cccaaaaacc aattgataat      240 caattttttac ttaaacttca aagaatgcct aacgtgataa tcacaccgca tacggcctat      300
tataccgagc aagcgttgcg tgataccgtt gaaaaaacca ttaaaaactg tttggatttt      360
gaaaggagac aggagcatga atagaataaa agttgcaata ctgtttgggg gttgctcaga      420
ggagcatgac gtatcggtaa atctgcaat agagatagcc gctaacatta ataaagaaaa       480
atacgagccg ttatacattg gaattacgaa atctggtgta tggaaaatgt gcgaaaaacc      540
ttgcgcggaa tgggaaaacg acaattgcta ttcagctgta ctctcgccgg ataaaaaaat      600
gcacggatta cttgttaaaa agaaccatga atatgaaatc aaccatgttg atgtagcatt      660
ttcagctttg catggcaagt caggtgaaga tggatccata caaggtctgt ttgaattgtc      720
cggtatccct tttgtaggct gcgatattca aagctcagca atttgtatgg acaaatcgtt      780
gacatacatc gttgcgaaaa atgctgggat agctactccc gccttttggg ttattaataa      840
agatgatagg ccggtggcag ctacgtttac ctatcctgtt tttgttaagc cggcgcgttc      900
aggctcatcc ttcggtgtga aaaagtcaa tagcgcggac gaattggact acgcaattga      960
atcggcaaga caatatgaca gcaaaatctt aattgagcag ctgtttcgg ctgtgaggt     1020 cggttgtgcg gtattgggaa acagtgccgc gttagttgtt ggcgaggtgg accaaatcag     1080
gctgcagtac ggaatctttc gtattcatca ggaagtcgag ccggaaaaag gctctgaaaa     1140
cgcagttata accgttcccg cagaccttc agcagaggag cgaggacgga tacaggaaac     1200
ggcaaaaaaa atatataaag cgctcggctg tagaggtcta gcccgtgtgg atatgttttt     1260
acaagataac ggccgcattg tactgaacga agtcaatact ctgcccggtt tcacgtcata     1320
cagtcgttat ccccgtatga tggccgctgc aggtattgca cttcccgaac tgattgaccg     1380
cttgatcgta ttagcgttaa aggggtgata agcatggaaa taggattta ctttttagat      1440 gaaatagtac acggtgttcg ttgggacgct aaatatgcca cttgggataa tttcaccgga     1500
aaaccggttg acggttatga agtaaatcgc attgtaggga catacgagtt ggctgaatcg     1560
```

-continued

| | |
|---|---|
| cttttgaagg caaaagaact ggctgctacc caagggtacg gattgcttct atgggacggt | 1620 |
| taccgtccta agcgtgctgt aaactgtttt atgcaatggg ctgcacagcc ggaaaataac | 1680 |
| ctgacaaagg aaagttatta tcccaatatt gaccgaactg agatgatttc aaaaggatac | 1740 |
| gtggcttcaa aatcaagcca tagccgcg | 1768 |

<210> SEQ ID NO 11
<211> LENGTH: 1768
<212> TYPE: DNA
<213> ORGANISM: Enterococcus faecium
<220> FEATURE:
<223> OTHER INFORMATION: vanA sequence

<400> SEQUENCE: 11

| | |
|---|---|
| gatatcgtta cgcttcatgt gccgctcaat acggatacgc actatattat cagccacgaa | 60 |
| caaatacaga gaatgaagca aggagcattt cttatcaata ctgggcgcgg tccacttgta | 120 |
| gatacctatg agttggttaa agcattagaa acgggaaaac tgggcggtgc cgcattggat | 180 |
| gtattggaag gagaggaaga gttttctac tctgattgca cccaaaaacc aattgataat | 240 |
| caattttac ttaaacttca aagaatgcct aacgtgataa tcacaccgca tacggcctat | 300 |
| tataccgagc aagcgttgcg tgataccgtt gaaaaaacca ttaaaaactg tttggatttt | 360 |
| gaaaggagac aggagcatga atagaataaa agttgcaata ctgtttgggg gttgctcaga | 420 |
| ggagcatgac gtatcggtaa atctgcaat agagatagcc gctaacatta ataaagaaaa | 480 |
| atacgagccg ttatacattg gaattacgaa atctggtgta tggaaaatgt gcgaaaaacc | 540 |
| ttgcgcggaa tgggaaaacg acaattgcta ttcagctgta ctctcgccgg ataaaaaaat | 600 |
| gcacggatta cttgttaaaa agaaccatga atatgaaatc aaccatgttg atgtagcatt | 660 |
| ttcagctttg catggcaagt caggtgaaga tggatccata caaggtctgt ttgaattgtc | 720 |
| cggtatccct tttgtaggct gcgatattca aagctcagca attgtatgg acaaatcgtt | 780 |
| gacatacatc gttgcgaaaa atgctgggat agctactccc gccttttggg ttattaataa | 840 |
| agatgatagg ccggtggcag ctacgtttac ctatcctgtt tttgttaagc cggcgcgttc | 900 |
| aggctcatcc ttcggtgtga aaaaagtcaa tagcgcggac gaattggact acgcaattga | 960 |
| atcggcaaga caatatgaca gcaaaatctt aattgagcag gctgtttcgg gctgtgaggt | 1020 |
| cggttgtgcg gtattgggaa acagtgccgc gttagttgtt ggcgaggtgg accaaatcag | 1080 |
| gctgcagtac ggaatctttc gtattcatca ggaagtcgag ccggaaaaag gctctgaaaa | 1140 |
| cgcagttata accgttcccg cagacctttc agcagaggag cgaggacgga tacaggaaac | 1200 |
| ggcaaaaaaa atatataaag cgctcggctg tagaggtcta gcccgtgtgg atatgttttt | 1260 |
| acaagataac ggccgcattg tactgaacga agtcaatact ctgcccggtt tcacgtcata | 1320 |
| cagtcgttat ccccgtatga tggccgctgc aggtattgca cttcccgaac tgattgaccg | 1380 |
| cttgatcgta ttagcgttaa aggggtgata agcatgaaa taggatttac tttttttagat | 1440 |
| gaaatagtac acgtgttcg ttgggacgct aaatatgcca cttgggataa tttcaccgga | 1500 |
| aaaccggttg acgttatga agtaaatcgc attgtaggga catacgagtt ggctgaatcg | 1560 |
| cttttgaagg caaaagaact ggctgctacc caagggtacg gattgcttct atgggacggt | 1620 |
| taccgtccta agcgtgctgt aaactgtttt atgcaatggg ctgcacagcc ggaaaataac | 1680 |
| ctgacaaagg aaagttatta tcccaatatt gaccgaactg agatgatttc aaaaggatac | 1740 |
| gtggcttcaa aatcaagcca tagccgcg | 1768 |

```
<210> SEQ ID NO 12
<211> LENGTH: 882
<212> TYPE: DNA
<213> ORGANISM: Enterococcus faecalis
<220> FEATURE:
<223> OTHER INFORMATION: vanB sequence

<400> SEQUENCE: 12
accaggcagg gtattgacct catttagaac gatgccgcca tcctcctgca aaaaaagatc      60
aacacgggca agccctctgc atccaagcac ccgatatact ttctttgccg tttcctgcac     120
ccgatttcgt tcctcgaccg gaatgtctgc gggaactgta atcatcgcat tttctgagcc     180
ttttccggc tcgttttcct gatggatgcg aagataccg tggctcagcc ggatttgatc      240
cacttcgccg acaatcaaat catcctcgtt ccccatgacc gcacacccga cctcacagcc     300
cgaaatcgct tgctcaatta agattttttcc atcatattgt cctgccgctt ctatcgcagc    360
gttaagttct tccgtaccgt ttactttggt tacgccaaag gacgaacctg accgtgccgg     420
cttcacaaag acagggtagg taagcgcacc cgcctccggc ttgtcacctt tatcaatcat     480
ttgaaattcg ggaacggcga tgcccgcatt ttttgtaaga atgtaggcca gtgatttgtc     540
catgcaagct gcggagcttt gaatatcgca gcctacatag gggataccag acaattcaaa    600
cagaccctgt atcgcaccat cctccccgca tttgccatgc aaaaccggga aagccacatc    660
aatacgccgt gtttcgtatt cgctttcttt catgacaagc agcccatgcg ttttcctatc    720
cggggagagt atggcgggga gactgtcggc ttcccattcc gtacatggct tcttgcatag   780
cttccatacg ccgttttttg taattccgat gtagtgcgga tcgaattttt cagtattaat    840
gttcgcagca atttctattg cggattttac cgacacatca tg                       882

<210> SEQ ID NO 13
<211> LENGTH: 556
<212> TYPE: DNA
<213> ORGANISM: Enterococcus faecium
<220> FEATURE:
<223> OTHER INFORMATION: vanB sequence

<400> SEQUENCE: 13 caaaaaaga tcaacacggg caagccctct gcatccaagc acccgatata ctttctttgc       60
cgtttcctgc acccgatttc gttcctcgac cggaatgtct gcgggaactg taatcatcgc     120
attttctgag cctttttccg gctcgttttc ctgatggatg cggaagatac cgtggctcag     180
ccggatttga tccacttcgc cgacaatcaa atcatcctcg ttccccatga ccgcacaccc     240
gacctcacag cccgaaatcg cttgctcaat taagattttt ccatcatatt gtcctgccgc     300
ttctatcgca gcgttaagtt cttccgtacc gtttactttg gttacgccaa ggacgaacc      360
tgaccgtgcc ggcttcacaa agacagggta ggtaagcgca cccgcctccg gcttgtcacc    420
tttatcaata atttgaaatt cgggaacggc gatgcccgca ttttttgtaa gaatgtaggc    480
cagtgatttg tccatgcaag ctgcggagct ttgaatatca gcccacat aggggatacc      540
agacaataca aacagc                                                    556

<210> SEQ ID NO 14
<211> LENGTH: 556
<212> TYPE: DNA
<213> ORGANISM: Enterococcus faecium
<220> FEATURE:
<223> OTHER INFORMATION: vanB sequence

<400> SEQUENCE: 14
```

```
caaaaaaaga tcaacacggg caagccctct gcatccaagc acccgatata ctttctttgc      60
cgtttcctgc acccgatttc gttcctcgac cggaatgtct gcgggaactg taatcatcgc     120
attttctgag cctttttccg gctcgttttc ctgatggatg cggaagatac cgtggctcag     180
ccggatttga tccacttcgc cgacaatcaa atcatcctcg ttccccatga ccgcacaccc     240
gacctcacag cccgaaatcg cttgctcaat taagattttt ccatcatatt gtcctgccgc     300
ttctatcgca gcgttaagtt cttccgtacc gtttactttg gttacgccaa aggacgaacc     360
tgaccgtgcc ggcttcacaa agacagggta ggtaagcgca cccgcctccg gcttgtcacc     420
tttatcaata atttgaaatt cgggaacggc gatgcccgca ttttttgtaa gaatgtaggc     480
cagtgatttg tccatgcaag ctgcggagct ttgaatatca cagcccacat aggggatacc     540
agacaataca aacagc                                                     556

<210> SEQ ID NO 15
<211> LENGTH: 556
<212> TYPE: DNA
<213> ORGANISM: Enterococcus faecium
<220> FEATURE:
<223> OTHER INFORMATION: vanB sequence

<400> SEQUENCE: 15
caaaaaaaga tcaacacggg caagccctct gcatccaagc acccgatata ctttctttgc      60
cgtttcctgc acccgatttc gttcctcgac cggaatgtct gcgggaactg taatcatcgc     120
attttctgag cctttttccg gctcgttttc ctgatggatg cggaagatac cgtggctcag     180
ccggatttga tccacttcgc cgacaatcaa atcatcctcg ttccccatga ccgcacaccc     240
gacctcacag cccgaaatcg cttgctcaat taagattttt ccatcatatt gtcctgccgc     300
ttctatcgca gcgttaagtt cttccgtacc gtttactttg gttacgccaa aggacgaacc     360
tgaccgtgcc ggcttcacaa agacagggta ggtaagcgca cccgcctccg gcttgtcacc     420
tttatcaatc atttgaaatt cgggaacggc gatgcccgca ttttttgtaa gaatgtaggc     480
cagtgatttg tccatgcaag ctgcggagct ttgaatatca cagcccacat aggggatacc     540
agacaataca aacagc                                                     556

<210> SEQ ID NO 16
<211> LENGTH: 556
<212> TYPE: DNA
<213> ORGANISM: Enterococcus faecium
<220> FEATURE:
<223> OTHER INFORMATION: vanB sequence

<400> SEQUENCE: 16
caaaaaaaga tcaacacggg caagccctct gcatccaagc acccgatata ctttctttgc      60
cgtttcctgc acccgatttc gttcctcgac cggaatgtct gcgggaactg taatcatcgc     120
attttctgag cctttttccg gctcgttttc ctgatggatg cggaagatac cgtggctcag     180
ccggatttga tccacttcgc cgacaatcaa atcatcctcg ttccccatga ccgcacaccc     240
gacctcacag cccgaaatcg cttgctcaat taagattttt ccatcatatt gtcctgccgc     300
ttctatcgca gcgttaagtt cttccgtacc gtttactttg gttacgccaa aggacgaacc     360
tgaccgtgcc ggcttcacaa agacagggta ggtaagcgca cccgcctccg gcttgtcacc     420
tttatcaata atttgaaatt cgggaacggc gatgcccgca ttttttgtaa gaatgtaggc     480
cagtgatttg tccatgcaag ctgcggagct ttgaatatca cagcccacat aggggatacc     540
agacaataca aacagc                                                     556
```

<210> SEQ ID NO 17
<211> LENGTH: 556
<212> TYPE: DNA
<213> ORGANISM: Enterococcus faecium
<220> FEATURE:
<223> OTHER INFORMATION: vanB sequence

<400> SEQUENCE: 17

| | | | | | |
|---|---|---|---|---|---|
| caaaaaaga | tcaacacgag | caagccctct | gcatccaagc | acccgatata | ctttctttgc | 60 |
| cgtttcttgc | acccgatttc | gttcctcgac | cggaatgtct | gctggaacga | taatcatcgc | 120 |
| attctctgag | ccttttttccg | gctcgttttc | ctgatggatg | cggaagatac | cgtggctcaa | 180 |
| ccggatttga | tccacttcgc | cgacaatcaa | atcatcctcg | tttcccatga | ccgcgcagcc | 240 |
| gacctcacag | cccgaaatcg | cttgctcaat | taagattttt | ccatcatatt | gtcctgctgc | 300 |
| ttctatcgca | gcgtttagtt | cttccgtact | gtttactttg | gttacgccaa | aggacgaacc | 360 |
| tgaccgtgcc | ggcttcacaa | agacagggta | ggtaagcgtc | ctcgcctccg | gtttgtcacc | 420 |
| tttttcaatc | atttgaaatt | cggggacggc | gatgcccgca | tttttttgtaa | gaatgtaggc | 480 |
| cagtgatttg | tccatgcaag | ctgcggagct | ttgaatatcg | cagcctacat | agggatacc | 540 |
| agacaattca | aacaga | | | | | 556 |

<210> SEQ ID NO 18
<211> LENGTH: 556
<212> TYPE: DNA
<213> ORGANISM: Enterococcus faecalis
<220> FEATURE:
<223> OTHER INFORMATION: vanB sequence

<400> SEQUENCE: 18

| | | | | | |
|---|---|---|---|---|---|
| caaaaaaga | tcaacacgag | caagccctct | gcatccaagc | acccgatata | ctttctttgc | 60 |
| cgtttcttgc | acccgatttc | gttcctcgac | cggaatgtct | gctggaacga | taatcatcgc | 120 |
| attctctgag | ccttttttccg | gctcgttttc | ctgatggatg | cggaagatac | cgtggctcaa | 180 |
| ccggatttga | tccacttcgc | cgacaatcaa | atcatcctcg | tttcccatga | ccgcgcagcc | 240 |
| gacctcacag | cccgaaatcg | cttgctcaat | taagattttt | ccatcatatt | gtcctgctgc | 300 |
| ttctatcgca | gcgtttagtt | cttccgtact | gtttactttg | gttacgccaa | aggacgaacc | 360 |
| tgaccgtgcc | ggcttcacaa | agacagggta | ggtaagcgtc | ctcgcctccg | gtttgtcacc | 420 |
| tttttcaatc | atttgaaatt | cggggacggc | gatgcccgca | tttttttgtaa | gaatgtaggc | 480 |
| cagtgatttg | tccatgcaag | ctgcggagct | ttgaatatcg | cagcctacat | agggatacc | 540 |
| agacaattca | aacaga | | | | | 556 |

<210> SEQ ID NO 19
<211> LENGTH: 556
<212> TYPE: DNA
<213> ORGANISM: Enterococcus faecalis
<220> FEATURE:
<223> OTHER INFORMATION: vanB sequence

<400> SEQUENCE: 19

| | | | | | |
|---|---|---|---|---|---|
| caaaaaaga | tcaacacggg | caagccctct | gcatccaagc | gcccgatata | ctttctttgc | 60 |
| cgtttcctgc | acccgatttc | gttccccgac | tgggatgtct | gcaggaacgg | taatcatcgc | 120 |
| attctctgat | ccttttttccg | gctcgttttc | ctgatggatg | cggaagatac | catggctcag | 180 |
| ccggatttga | tccacttcgc | cgacaatcaa | atcatcctcg | ttcccataa | ccgcacagcc | 240 |

-continued

```
gacctcacag cccgaaatcg cttgctcaat taagattttt ccatcatatt gtcctgccgc      300
ttctatcgca gcgttaagtt cttccgtacc gtttactttg gttaagccaa aggacgaacc      360
tgaccgtgcc ggcttcacaa agacagggta ggtaagcgca cccgtctccg gcttgtcacc      420
tttatcaatc atttgaaatt cgggaacggc gatgcccgca ttttttgtaa gaatgtaggc      480
cagtgatttg tccatgcaag ctgcggagct ttgaatatcg cagcccacat aggggatgcc      540
agacaattca aataaa                                                      556
```

<210> SEQ ID NO 20
<211> LENGTH: 556
<212> TYPE: DNA
<213> ORGANISM: Enterococcus faecalis
<220> FEATURE:
<223> OTHER INFORMATION: vanB sequence

<400> SEQUENCE: 20

```
caaaaaaga tcaacacggg caagccctct gcatccaagc acccgatata ctttctttgc       60
cgtttcctgc acccgatttc gttcctcgac cggaatgtct gcgggaactg taatcatcgc     120
attttctgag ccttttccg gctcgttttc ctgatggatg cggaagatac cgtggctcag     180
ccggatttga tccacttcgc cgacaatcaa atcatcctcg ttccccatga ccgcacaccc     240
gacctcacag cccgaaatcg cttgctcaat taagattttt ccatcatatt gtcctgccgc     300
ttctatcgca gcgttaagtt cttccgtacc gtttactttg gttacgccaa aggacgaacc     360
tgaccgtgcc ggcttcacaa agacagggta ggtaagcgca cccgcctccg gcttgtcacc     420
tttatcaatc atttgaaatt cgggaacggc gatgcccgca ttttttgtaa gaatgtaggc     480
cagtgatttg tccatgcaag ctgcggagct ttgaatatca cagcccacat aggggatacc     540
agacaattca aacagt                                                     556
```

DETECTION OF VANCOMYCIN-RESISTANT ENTEROCOCCUS SPP.

TECHNICAL FIELD

This invention relates to bacterial diagnostics, and more particularly to detection of vancomycin-resistant *Enterococcus* spp.

BACKGROUND

*Enterococci* are Gram-positive cocci that are considered normal inhabitants of the gastrointestinal tract and the female genital tract. *Enterococcus* spp. are not particularly pathogenic in humans, but vancomycin-resistant *enterococci* have been increasingly identified as an important cause of hospital acquired infection. Vancomycin-resistant *enterococci* have been recognized as the second most common cause of hospital infection, exceeded only by *E. coli*. *Enterococcus faecalis* (85–90%) and *E. faecium* (5–10%) are the species of *Enterococci* most commonly isolated from the gastrointestinal tracts of humans and represent the majority of the vancomycin-resistant *enterococci*.

SUMMARY

The invention provides for methods of identifying vancomycin-resistant *enterococci* in a biological sample. Primers and probes for detecting nucleic acids encoding vanA, vanB, or vanB-2/3 are provided by the invention, as are kits containing such primers and probes. Methods of the invention can be used to rapidly identify nucleic acids from vancomycin-resistant *enterococci* from samples. Using specific primers and probes, the methods include amplifying and monitoring the development of specific amplification products using real-time PCR.

In one aspect of the invention, there is provided a method for detecting the presence or absence of one or more vancomycin-resistant nucleic acids in a biological sample from an individual. The method to detect vancomycin-resistant *enterococci* includes performing at least one cycling step, which includes an amplifying step and a hybridizing step. The amplifying step includes contacting the sample with a pair of vanA primers to produce an amplification product if a vanA nucleic acid molecule is present in the sample. The hybridizing step includes contacting the sample with a pair of vanA probes. Generally, the members of the pair of vanA probes hybridize to the amplification product within no more than five nucleotides of each other. A first vanA probe of the pair of vanA probes is typically labeled with a donor fluorescent moiety and a second vanA probe of the pair of vanA probes is typically labeled with a corresponding acceptor fluorescent moiety. The method further includes detecting the presence or absence of fluorescence resonance energy transfer (FRET) between the donor fluorescent moiety of the first vanA probe and the acceptor fluorescent moiety of the second vanA probe. The presence of FRET is usually indicative of the presence of one or more vancomycin-resistant *enterococci* in the biological sample, while the absence of FRET is usually indicative of the absence of the vancomycin-resistant *enterococci* in the biological sample.

Alternatively or additionally, the amplifying step can include contacting the sample with a pair of vanB primers to produce a vanB amplification product if a vanB nucleic acid molecule is present in the sample. The hybridizing step includes contacting the sample with a pair of vanB probes. Generally, the members of the pair of vanB probes hybridize to the amplification product within no more than five nucleotides of each other. A first vanB probe of the pair of vanB probes is typically labeled with a donor fluorescent moiety and a second vanB probe of the pair of vanB probes is typically labeled with a corresponding acceptor fluorescent moiety. The method further includes detecting the presence or absence of FRET between the donor fluorescent moiety of the first vanB probe and the acceptor fluorescent moiety of the second vanB probe. The presence of FRET usually indicates the presence of one or more vancomycin-resistant *enterococci* in the biological sample, and the absence of FRET usually indicates the absence of a vancomycin-resistant *enterococci* in the biological sample.

A pair of vanA primers generally includes a first vanA primer and a second vanA primer. The first vanA primer can include the sequence 5'-CGA GGA CGG ATA CAG GA-3' (SEQ ID NO:1), and the second vanA primer can include the sequence 5'-CTT ATC ACC CCT TTA ACG C-3' (SEQ ID NO:2). A first vanA probe can include the sequence 5'-CAA GAT AAC GGC CGC ATT GTA CTG AAC GA-3' (SEQ ID NO:3), and the second vanA probe can include the sequence 5'-GTC AAT ACT CTG CCC GGT TTC AC-3' (SEQ ID NO:4).

A pair of vanB/vanB-2/3 primers generally includes a first vanB/vanB-2/3 primer and a second vanB/vanB-2/3 primer. A first vanB vanB-2/3 primer can include the sequence 5'-GAA GAT ACC GTG GCT CA-3' (SEQ ID NO:5), and the second vanB/vanB-2/3 primer can include the sequence 5'-GTA CGG AAG AAC TTA ACG CT-3' (SEQ ID NO:6). A first vanB/vanB-2/3 probe can include the sequence 5'-GAT CCA CTT CGC CGA CAA-3' (SEQ ID NO:7), and the second vanB/vanB-2/3 probe can include the sequence 5'-AAA TCA TCC TCG TTT CCC AT-3' (SEQ ID NO:8).

In some aspects, one of the vanA or vanB/vanB-2/3 primers can be labeled with a fluorescent moiety (either a donor or acceptor, as appropriate) and can take the place of one of the vanA or vanB/vanB-2/3 probes, respectively.

The members of the pair of vanA probes or vanB/vanB-2/3 probes can hybridize within no more than two nucleotides of each other, or can hybridize within no more than one nucleotide of each other. A representative donor fluorescent moiety is fluorescein, and corresponding acceptor fluorescent moieties include LC-Red 640, LC-Red 705, Cy5, and Cy5.5. Additional corresponding donor and acceptor fluorescent moieties are known in the art.

In one aspect, the detecting step includes exciting the biological sample at a wavelength absorbed by the donor fluorescent moiety and visualizing and/or measuring the wavelength emitted by the acceptor fluorescent moiety (i.e., visualizing and/or measuring FRET). In another aspect, the detecting comprises quantitating the FRET. In yet another aspect, the detecting step can be performed after each cycling step (i.e., in real-time).

Generally, the presence of FRET within 50 cycles (e.g., 20, 25, 30, 35, 40, or 45 cycles) indicates the presence of one or more vancomycin-resistant *enterococci* in the individual. In addition, determining the melting temperature between one or both of the vanA probe(s) and the amplification product, wherein the melting temperature confirms the presence or the absence of a vancomycin-resistant *enterococci*, while determining the melting temperature between one or both of the vanB/vanB-2/3 probe(s) and the vanB/vanB-2/3 amplification product also confirms the presence or the absence of particular vancomycin-resistant *enterococci*.

Representative biological samples include anal or perirectal swabs, stool samples, blood, and body fluids. The above-described methods can further include preventing amplification of a contaminant nucleic acid. Preventing amplification of a contaminant nucleic acid can include performing the amplifying step in the presence of uracil and treating the biological sample with uracil-DNA glycosylase prior to amplifying.

In addition, the cycling step can be performed on a control sample. A control sample can include a vanA, vanB, or vanB-2/3 nucleic acid molecule. Alternatively, a control sample can include a nucleic acid molecule other than a vanA, vanB or vanB-2/3 nucleic acid molecule. Cycling steps can be performed on such a control sample using a pair of control primers and a pair of control probes. The control primers and the control probes are other than the vanA or vanB/vanB-2/3 primers and probes. One or more amplifying steps can produce a control amplification product. Each of the control probes hybridizes to the control amplification product.

In another aspect of the invention, there are provided articles of manufacture, or kits. Kits of the invention can include a pair of vanA primers; a pair of vanA probes; and a donor fluorescent moiety and a corresponding fluorescent moiety. For example, a first vanA primer provided in a kit of the invention can include the sequence 5'-CGA GGA CGG ATA CAG GA-3' (SEQ ID NO:1), and the second vanA primer can include the sequence 5'-CTT ATC ACC CCT TTA ACG C-3' (SEQ ID NO:2). A first vanA probe can include the sequence 5'-CAA GAT AAC GGC CGC ATT GTA CTG AAC GA-3' (SEQ ID NO:3), and the second vanA probe can include the sequence 5'-GTC AAT ACT CTG CCC GGT TTC AC-3' (SEQ ID NO:4).

Articles of manufacture of the invention can further or alternatively include a pair of vanB/vanB-2/3 primers; a pair of vanB/vanB-2/3 probes; and a donor fluorescent moiety and a corresponding fluorescent moiety. For example, the first vanB/vanB-2/3 primer provided in a kit of the invention can include the sequence 5'-GAA GAT ACC GTG GCT CA-3' (SEQ ID NO:5), and the second vanB/vanB-2/3 primer can include the sequence 5'-GTA CGG AAG AAC TTA ACG CT-3' (SEQ ID NO:6). The first vanB/vanB-2/3 probe provided in a kit of the invention can include the sequence 5'-GAT CCA CTT CGC CGA CAA-3' (SEQ ID NO:7), and the second vanB/vanB-2/3 probe can include the sequence 5'-AAA TCA TCC TCG TTT CCC AT-3' (SEQ ID NO:8).

Articles of the invention can include fluorophoric moieties for labeling the probes, or probes already labeled with donor and corresponding acceptor fluorescent moieties. The article of manufacture can also include a package label or package insert having instructions thereon for using the pair of vanA primers and the pair of vanA probes to detect the presence or absence of one or more vancomycin-resistant *enterococci* in a biological sample, or for using the pair of vanB/vanB-2/3 primers and the pair of vanB/vanB-2/3 probes to detect the presence or absence of one or more vancomycin-resistant *enterococci* in a biological sample.

In yet another aspect of the invention, there is provided a method for detecting the presence or absence of one or more vancomycin-resistant *enterococci* in a biological sample from an individual. Such a method includes performing at least one cycling step. A cycling step can include an amplifying step and a hybridizing step. Generally, an amplifying step includes contacting the sample with a pair of vanA primers to produce an amplification product if a vanA nucleic acid molecule is present in the sample. Generally, a hybridizing step includes contacting the sample with a vanA probe. Such a vanA probe is usually labeled with a donor fluorescent moiety and a corresponding acceptor fluorescent moiety. The method further includes detecting the presence or absence of FRET between the donor fluorescent moiety and the acceptor fluorescent moiety of the vanA probe. The presence or absence of FRET is indicative of the presence or absence of one or more vancomycin-resistant *enterococci* in the sample.

In one aspect, amplification can employ a polymerase enzyme having 5' to 3' exonuclease activity. Thus, the donor and acceptor fluorescent moieties would be within no more than 5 nucleotides of each other along the length of the probe. In another aspect, the vanA probe includes a nucleic acid sequence that permits secondary structure formation. Such secondary structure formation generally results in spatial proximity between the donor and the acceptor fluorescent moiety. According to this method, the acceptor fluorescent moiety is a quencher.

In another aspect of the invention, there is provided a method for detecting the presence or absence of one or more vancomycin-resistant *enterococci* in a biological sample from an individual. Such a method includes performing at least one cycling step. A cycling step can include an amplifying step and a dye-binding step. An amplifying step generally includes contacting the sample with a pair of vanA primers to produce an amplification product if a vanA nucleic acid molecule is present in the sample. A dye-binding step generally includes contacting the amplification product with a double-stranded nucleic acid binding dye. The method further includes detecting the presence or absence of binding of the double-stranded nucleic acid binding dye to the amplification product. According to the invention, the presence of binding is typically indicative of the presence of one or more vancomycin-resistant *enterococci* in the sample, and the absence of binding is typically indicative of the absence of a vancomycin-resistant *enterococci* in the sample. Such a method can further include the steps of determining the melting temperature between the amplification product and the double-stranded nucleic acid binding dye. Generally, the melting temperature confirms the presence or absence of vancomycin-resistant *enterococci*. Representative double-stranded nucleic acid binding dye include SYBRGreenI®, SYBRGold®, and ethidium bromide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF THE DRAWINGS

FIG. 1 is an alignment of vanA nucleic acid sequences.

FIG. 2 is an alignment of vanB nucleic acid sequences.

DETAILED DESCRIPTION

A real-time PCR assay that is more sensitive than existing assays is described herein for detecting vancomycin-resistant *enterococci* in a biological sample such as a fecal sample. Primers and probes for detecting vanA, vanB, and/or vanB-2/3 nucleic acids are provided by the invention, as are articles of manufacture containing such primers and probes. The assay for vancomycin-resistant *enterococci* was designed to discriminate between the vanA, vanB and vanB-2/3 genotypes based on a difference in melting temperature between a pair of vanA probes and a pair of vanB probes. The increased sensitivity of the real-time PCR assay for detecting vancomycin-resistant *enterococci* nucleic acids compared to other methods, as well as the improved features of real-time PCR including sample containment and real-time detection of the amplified product, make feasible the implementation of this technology for routine clinical laboratory for the detection of vancomycin-resistant *enterococci*.

The total time for processing a sample using the LIGHT-CYCLER™ vancomycin-resistant *Enteroccocus* assay is less than 3 hrs compared to 4–7 days for detection by routine culture. The invention has the potential to replace standard culture methods which require select media, biochemical testing, and susceptibility testing and therefore, result in cost savings to institutions. Since clinicians receive a single test result within a few hours, appropriate isolation procedures and antimicrobial therapy can begin almost immediately. The rapid vancomycin-resistant *Enteroccocus* real-time PCR assay allows hospitals to take the necessary precautions with vancomycin-resistant *enterococci*-infected patients such that the spread of vancomycin-resistant *enterococci* to other patients is prevented.

*Enterococcus* spp.

*Enterococcus* spp. have the characteristic of being resistant to many antimicrobial agents, which make them formidable pathogens and limit the therapeutic options available to the clinician. All *enterococci* are intrinsically resistant to a number of antibiotics and exhibit low levels of resistance to the β-lactam agents, the aminogycosides, and the lincosamides. They have acquired genes of resistance to all known antimicrobial agents, including the glycopeptides vancomycin and teicoplanin. One of the concerns is the possibility that the vancomycin-resistant genes may be transferred to other Gram-positive organisms, especially *Staphylococcus aureus*.

A BLAST alignment of vanA sequences found no other organisms containing sequences similar to vanA. A BLAST alignment of vanB sequences showed that vanB sequences can be found in *Enterococcus* spp. and animal species (veal calves) of streptococci such as *S. gallolyticus* and *S. infantarius* (Genebank Accession Nos. AY035705 and Z70527). One other isolate, *S. bovis*, also has sequences that exhibit homology to vanB sequences. These streptococcus isolates appear to have acquired enterococcal vanB vancomycin resistance genes.

Vancomycin-resistant *enterococci* exhibit optimal growth at 35° C. and will grow in 6.5% NaCl. Vancomycin-resistant *enterococci* are able to hydrolyze esculin. Vancomycin-resistant *enterococci* are selectively cultured on *Enterococcosel* agar containing 8 µg/ml vancomycin. The glycopeptide resistance of vancomycin-resistant *enterococci* has three different phenotypes. vanA is the most frequently isolated phenotype with high levels of resistance to vancomycin and teicoplanin. The vanB phenotypes (e.g., vanB, or vanB-2/3) has variable vancomycin-resistance and is susceptible to teicoplanin. The vanC phenotype has low levels of vancomycin-resistance and is susceptible to teicoplanin and is therefore less important for detection by a clinical laboratory.

PCR-RFLP assays following Msp1 restriction digestion can be used to differentiate the vanA genotype from the vanB genotype. The vanA strains typically exhibit a high level of vancomycin resistance (minimum inhibitory concentration (MIC)>64 µg/ml). vanA strains also exhibit inducible resistance to vancomycin and teicoplanin. The genes encoding vanA are located on a transposon or a plasmid, and are easily transferred by conjugation. The first vanA strain of vancomycin-resistant *enterococci* was reported in 1986, and represents approximately 70% of vancomycin-resistant *enterococci* isolates from patient specimens. On the other hand, vanB strains exhibit variable resistance to vancomycin (MIC 4 to >1024 µg/ml), and exhibit inducible resistance to vancomycin only. The genes encoding vanB are chromosomal and can be transferred by conjugation. vanB strains were first identified in the U.S. in 1987, and currently make up about 25% of the vancomycin-resistant patient isolates.

Vancomycin-Resistant *Enterococci* Nucleic Acids and Oligonucleotides

The invention provides methods to detect vanA, vanB, and/or van-B2/3 nucleic acids by amplifying, for example, nucleic acid molecules corresponding to a portion of vanA, vanB, and/or vanB-2/3. Nucleic acid molecules other than those exemplified herein (e.g., other than vanA, vanB, and/or vanB-2/3) also can be used to detect vancomycin-resistant *enterococci* in a sample and are known to those of skill in the art. vanA, vanB, and vanB-2/3 nucleic acid sequences have been described (see, for example, GenBank Accession Nos. M97297, U94528, and U72704). Specifically, primers and probes to amplify and detect vanA, vanB, and/or vanB-2/3 nucleic acids are provided by the invention.

Primers that amplify a vanA, vanB, and/or vanB-2/3 nucleic acid molecule, e.g., nucleic acids encoding a portion of vanA, vanB, and/or vanB-2/3, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "vanA primers", "vanB primers", or "vanB2/3 primers" as used herein refer to oligonucleotide primers that anneal to vanA, vanB, and/or vanB2/3 nucleic acid sequences, respectively, and initiate synthesis therefrom under appropriate conditions.

Designing oligonucleotides to be used as hybridization probes can be performed in a manner similar to the design of primers, although the members of a pair of probes preferably anneal to an amplification product within no more than 5 nucleotides of each other on the same strand such that fluorescent resonance energy transfer (FRET) can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a mutation or polymorphism, thereby allowing differential detection of vancomycin-resistant *enterococci* based on either absolute hybridization of different pairs of probes corresponding to each particular *enterococci* to be distinguished or differential melting temperatures between, for example, members of a pair of probes and each amplification product generated from a vancomycin-resistant *enterococci*. As with oligonucleotide primers, oligonucleotide probes usually have similar melting temperatures, and the length of each probe must be sufficient for sequence-specific hybridization to occur but not so long that fidelity is reduced during synthesis. Oligonucleotide probes typically are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "vanA probes" as used herein refers to oligonucleotide probes that specifically anneal to vanA amplification products. As used herein, "vanB/vanB-2/3 probes" refer to oligonucleotide probes that anneal to either vanB or vanB-2/3, which can be differentiated based upon the melting temperature of the vanB/vanB-2/3 probes with the respective (i.e., vanB or vanB-2/3) amplification product.

Constructs of the invention include vectors containing a vanA, vanB, and/or vanB-2/3 nucleic acid molecule, e.g., a vanA, vanB, and/or vanB-2/3 gene, or fragment thereof. Constructs can be used, for example, as control template nucleic acids. Vectors suitable for use in the present invention are commercially available or can be produced by recombinant DNA technology methods routine in the art. A vanA, vanB, and/or vanB-2/3 nucleic acid molecule can be obtained, for example, by chemical synthesis, direct cloning from a vancomycin-resistant *enterococci*, or by PCR amplification. A vancomycin-resistant *Enterococcus* nucleic acid molecule or fragments thereof can be operably linked to a promoter or other regulatory element such as an enhancer sequence, a response element or an inducible element that modulates expression of the *Enterococcus* nucleic acid molecule. As used herein, operably linking refers to connecting a promoter and/or other regulatory elements to an *Enterococcus* nucleic acid molecule in such a way as to permit and/or regulate expression of the nucleic acid molecule. A promoter that does not normally direct expression of vanA, vanB, and/or vanB-2/3 can be used to direct transcription of a vanA, vanB, and/or vanB-2/3 nucleic acid molecule using, for example a viral polymerase, a bacterial polymerase, or a eukaryotic RNA polymerase. Alternatively, a vanA, vanB, and/or vanB-2/3 native promoter can be used to direct transcription of a vanA, vanB, and/or vanB-2/3 nucleic acid molecule using, for example, an *E. coli* RNA polymerase or a host RNA polymerase. In addition, operably linked can refer to an appropriate connection between a vanA, vanB, and/or vanB-2/3 promoter or other regulatory element to a heterologous coding sequence (i e., a non-vanA, -vanB, and/or -vanB-2/3 coding sequence, for example a reporter gene) in such a way as to permit expression of the heterologous coding sequence.

Constructs suitable for use in the methods of the invention typically include, in addition to a vanA, vanB, and/or vanB-2/3 nucleic acid molecule, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing a vanA, vanB, and/or vanB-2/3 nucleic acid molecule can be propagated in a host cell. As used herein, the term host cell is meant to include prokaryotes and eukaryotes. Prokaryotic hosts can include *E. coli, Salmonella typhimurium, Serratia marcescens* and *Bacillus subtilis*. Eukaryotic hosts include yeasts such as *S. cerevisiae, S. pombe*, and *Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as points of initiation of nucleic acid synthesis within a vancomycin-resistant *enterococci* nucleic acid sequence. A primer can be purified from a restriction digest by conventional methods, or it can be produced synthetically. A primer is preferably single-stranded for maximum efficiency in amplification, but a primer can be double-stranded. Double-stranded primers are first denatured, i.e., treated to separate the strands. One method of denaturing double-stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR provided the enzyme is replenished.

If the nucleic acid template is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 0 sec to 4 min.

If the double-stranded nucleic acid is denatured by heat, the reaction mixture is allowed to cool to a temperature that promotes annealing of each primer to its target sequence on the vancomycin-resistant *enterococci* nucleic acid. The temperature for annealing is usually from about 35° C. to about 65° C. The reaction mixture is then adjusted to a temperature at which the activity of the polymerase is promoted or optimized, e.g., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template. The temperature generally ranges from about 40° to 80° C.

PCR assays can employ nucleic acid template such as DNA or RNA, including messenger RNA (mRNA). The template nucleic acid need not be purified; it may be a minor fraction of a complex mixture, such as vancomycin-resistant *Enterococcus* nucleic acid contained in human cells. DNA or RNA may be extracted from any biological sample such as stool, anal or perirectal swabs, or body fluids (e.g., blood or urine) by routine techniques such as those described in *Diagnostic Molecular Microbiology: Principles and Applications* (Persing et al. (eds), 1993, American Society for Microbiology, Washington D.C.). vanA, vanB, and/or vanB-2/3 nucleic acids to be used as controls can be obtained from any number of sources, such as plasmids, or natural sources including bacteria, yeast, viruses, organelles, or higher organisms such as plants or animals.

The oligonucleotide primers are combined with other PCR reagents under reaction conditions that induce primer extension. For example, chain extension reactions generally include 50 mM KCl, 10 mM Tris-HCl (pH 8.3), 1.5 mM $MgCl_2$, 0.001% (w/v) gelatin, 0.5–1.0 µg denatured template DNA, 50 pmoles of each oligonucleotide primer, 2.5 U of Taq polymerase, and 10% DMSO. The reactions usually contain 150 to 320 µM each of dATP, dCTP, dTTP, dGTP, or one or more analogs thereof. In certain circumstances, 300 to 640 µM dUTP can be substituted for dTTP in the reaction.

The newly synthesized strands form a double-stranded molecule that can be used in the succeeding steps of the reaction. The steps of strand separation, annealing, and elongation can be repeated as often as needed to produce the desired quantity amplification products corresponding to the target vancomycin-resistant *enterococci* nucleic acid molecule. The limiting factors in the reaction are the amounts of primers, thermostable enzyme, and nucleoside triphosphates present in the reaction. The cycling steps (i.e., amplification and hybridization) are preferably repeated at least once. For use in detection, the number of cycling steps will depend, e.g., on the nature of the sample. If the sample is a complex mixture of nucleic acids, more cycling steps may be required to amplify the target sequence sufficient for detection. Generally, the cycling steps are repeated at least about 20 times, but may be repeated as many as 40, 60, or even 100 times.

Fluorescent Resonance Energy Transfer (FRET)

FRET technology (see, for example, U.S. Pat. Nos. 4,996, 143, 5,565,322, 5,849,489, and 6,162,603) is based on the fact that when a donor and a corresponding acceptor fluorescent moiety are positioned within a certain distance of each other, energy transfer takes place between the two fluorescent moieties that can be visualized or otherwise detected and/or quantitated. As used herein, two oligonucleotide probes, each containing a fluorescent moiety, can hybridize to an amplification product at particular positions determined by the complementarity of the oligonucleotide probes to the vancomycin-resistant *enterococci* target nucleic acid sequence. Upon hybridization of the oligonucleotide probes to the amplification product at the appropriate positions, a FRET signal is generated.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety preferably should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-Red 640, LC™-Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm can be important, as the linker arms will affect the distance between the donor and the acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to particular nucleotide bases, and also for attaching fluorescent moieties to a linker arm.

An acceptor fluorescent moiety such as an LC™-Red 640-NHS-ester can be combined with C6-Phosphoramidites (available from ABI (Foster City, Calif.) or Glen Research (Sterling, Va.)) to produce, for example, LC™-Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of Vancomycin-Resistant *Enterococci*

In the hospital laboratory, routine culture for the detection of vancomycin-resistant *Enterococcus* from stool or anal swabs using selective media is a reliable method but may require up to 4–7 days for identification. Culture methods are also time consuming and expensive for laboratories performing a large number of specimens. For recovery of vancomycin-resistant *enterococci* in the laboratory, a selective medium containing vancomycin at a concentration of 8 μg/ml in agar is used. This medium also contains bile esculin, which is hydrolyzed to impart a black-brown color to *Enterococcus* colonies. Identification of suspect colonies and antimicrobial susceptibility tests are performed on *Enterococcus* spp., which also can take several days to perform.

The invention provides methods for detecting the presence or absence of one or more vancomycin-resistant *enterococci* in a biological sample from an individual. Methods provided by the invention avoid problems of sample contamination, false negatives and false positives. The methods include performing at least one cycling step that includes amplifying and hybridizing. An amplification step includes contacting the biological sample with a pair of vanA, vanB, and/or vanB-2/3 primers to produce an amplification product if nucleic acid molecules from one or more vancomycin-resistant *enterococci* are present in the sample. Each of the vanA, vanB, and/or vanB-2/3 primers anneals to a target within or adjacent to a vanA, vanB, and/or vanB-2/3 nucleic acid molecule, respectively, such that at least a portion of the amplification product contains nucleic acid sequence corresponding to the respective vancomycin-resistant *enterococci* nucleic acid, and, more importantly, such that the amplification product contains the nucleic acid sequences that are complementary to vanA, vanB, and/or vanB-2/3 probes. A hybridizing step includes contacting the sample with a pair of vanA, vanB, and/or vanB2/3 probes. Generally, the members of the pair of vanA, vanB, and/or vanB-2/3 probes hybridize to the appropriate amplification product within no more than five nucleotides of each other. According to the invention, a first vanA, vanB, and/or vanB-2/3 probe of the pair of vanA, vanB, and/or vanB-2/3 probes, respectively, is labeled with a donor fluorescent moiety and a second vanA, vanB, and/or vanB-2/3 probe of the pair of vanA, vanB, and/or vanB-2/3 probes, respectively, is labeled with a corresponding acceptor fluorescent moiety. The method further includes detecting the presence or absence of FRET between the donor fluorescent moiety of the first vanA, vanB, and/or vanB-2/3 probe and the corresponding acceptor fluorescent moiety of the second vanA, vanB, and/or vanB-2/3 probe. Multiple cycling steps can be performed, preferably in a thermocycler. The above-described methods for detecting vancomycin-resistant *Enterococcus* in a biological sample using primers and probes directed toward vanA, vanB, and/or vanB-2/3 also can be performed using other vancomycin-resistant *Enterococcus* gene-specific primers and probes.

As used herein, "amplifying" refers to the process of synthesizing nucleic acid molecules that are complementary to one or both strands of a template nucleic acid (e.g., vanA, vanB, and/or vanB-2/3 nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times such that the amount of amplification product is increasing, oftentimes exponentially, although exponential amplification is not required by the present methods. Amplification typically requires the presence of deoxyribonucleoside triphosphates, a DNA polymerase enzyme (e.g., PLATINUM® TAQ) and an appropriate buffer and/or co-factors for optimal activity of the polymerase enzyme (e.g., $MgCl_2$ and/or KCl).

If amplification of vancomycin-resistant *enterococci* nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of vancomycin-resistant *enterococci* in the biological sample, and the absence of FRET indicates the absence of a vancomycin-resistant *enterococci* in the biological sample. Inadequate specimen collection, transportation delays, inappropriate transportation conditions, or use of certain collection swabs (e.g., calcium alginate or aluminum shaft) are all conditions that can affect the success and/or accuracy of the test result, however. Using the methods disclosed herein, detection of FRET within 45 cycling steps is indicative of one or more vancomycin-resistant *enterococci*.

Representative biological samples that can be used in practicing the methods of the invention include anal or perirectal swabs, stool samples, blood, or body fluids. Biological sample collection and storage methods are known to those of skill in the art. Biological samples can be processed (e.g., by standard nucleic acid extraction methods and/or using commercial kits) to release nucleic acid encoding vancomycin-resistance or, in some cases, the biological sample is contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides.

By detecting the temperature at which signal is lost, the melting temperature of probes can be determined. Similarly, by detecting the temperature at which signal is generated, the annealing temperature of probes can be determined. The melting temperature(s) of the vanA, vanB, and/or vanB-2/3 probes from the respective amplification product, respectively, can confirm the presence of one or more vancomycin-resistant *enterococci* in the sample.

Within each thermocycler run, control samples can be cycled as well. Control nucleic acid template can be amplified from a positive control sample (e.g., template other than vanA vanB, and/or vanB-2/3) using, for example, control primers and control probes. Positive control samples can also be used to amplify, for example, a plasmid construct containing a vancomycin-resistant *enterococci* nucleic acid molecule. Such a plasmid control can be amplified internally (e.g., within each biological sample) or in separate samples run side-by-side with the patients' samples. Each thermocycler run also should include a negative control that, for example, lacks vancomycin-resistant *enterococci* template nucleic acid. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

In one embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are desirable for accuracy in a diagnostic laboratory handling clinical samples.

Conventional PCR methods in conjunction with FRET technology can be used to practice the methods of the invention. In one embodiment, a LIGHTCYCLER™ instrument is used. A detailed description of the LIGHTCYCLER™ System and real-time and on-line monitoring of PCR can be found at biochem.roche.com/lightcycler on the World Wide Web. The following patent applications describe real-time PCR as used in the LIGHTCYCLER™ technology: WO 97/46707, WO 97/46714 and WO 97/46712. The LIGHTCYCLER™ instrument is a rapid thermocycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LIGHTCYCLER™ thermal chamber. Addition of selected fluorescent dyes to the reaction components allows the PCR to be monitored in real-time and on-line. Furthermore, the cuvettes serve as an optical element for signal collection (similar to glass fiber optics), concentrating the signal at the tip of the cuvettes. The effect is efficient illumination and fluorescent monitoring of microvolume samples.

The LIGHTCYCLER™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LIGHTCYCLER™ apparatus, houses the light source. The emitted light is filtered and focused by an epi-illumination lens onto the top of the cuvettes. Fluorescent light emitted from the sample is then focused by the same lens, passed through a dichroic mirror, filtered appropriately, and focused onto data-collecting photohybrids. The optical unit currently available in the LIGHTCYCLER™ instrument (Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LIGHTCYCLER™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10–100 msec. After each cycling step, a quantitative display of fluorescence vs. cycle number can be continually updated for all samples. The data generated can be stored for further analysis.

A common FRET technology format utilizes two hybridization probes. Each probe can be labeled with a different fluorescent moiety and the two probes are generally designed to hybridize in close proximity to each other in a target DNA molecule (e.g., an amplification product). By way of example, a donor fluorescent moiety such as fluorescein can be excited at 470 nm by the light source of the LIGHTCYCLER™ Instrument. During FRET, fluorescein transfers its energy to an acceptor fluorescent moiety such as LIGHTCYCLER™-Red 640 (LC™-Red 640) or LIGHT-CYCLER™-Red 705 (LC™-Red 705). The acceptor fluorescent moiety then emits light of a longer wavelength (e.g., 640 nm or 705 nm, respectively), which is detected by the optical detection system of the LIGHTCYCLER™ instrument. Other donor and corresponding acceptor fluorescent moieties suitable for use in the invention are described above. Efficient FRET can only take place when the fluorescent moieties are in direct local proximity (for example, within 5 nucleotides of each other as described above) and when the emission spectrum of the donor fluorescent moiety overlaps with the absorption spectrum of the acceptor fluorescent moiety. The intensity of the emitted signal can be correlated with the number of original target DNA molecules (e.g., the number of vancomycin-resistant *enterococci*).

Another FRET technology format utilizes TAQMAN® technology to detect the presence or absence of an amplification product, and hence, the presence or absence of vancomycin-resistant *enterococci*. TAQMAN® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TAQ-MAN® technology, and is suitable for performing the methods described herein for detecting vancomycin-resistant *enterococci*. Information on PCR amplification and detection using an ABI PRISM® 770 system can be found at appliedbiosystems.com/products on the World Wide Web.

Yet another FRET technology format utilizes molecular beacon technology to detect the presence or absence of an amplification product, and hence, the presence or absence of one or more vancomycin-resistant *enterococci*. Molecular beacon technology uses a hybridization probe labeled with a donor fluorescent moiety and an acceptor fluorescent moiety. The acceptor fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., the amplification products), the secondary structure of the probe is disrupted and the fluorescent moieties become separated from one another such that after excitation with light of a suitable wavelength, the emission of the first fluorescent moiety can be detected.

As an alternative to detection using FRET technology, an amplification product can be detected using a nucleic acid binding dye such as a fluorescent DNA binding dye (e.g., SYBRGreenI® or SYBRGold® (Molecular Probes)). Upon interaction with the double-stranded nucleic acid, such nucleic acid binding dyes emit a fluorescence signal after excitation with light at a suitable wavelength. A nucleic acid binding dye such as a nucleic acid intercalating dye also can be used. When nucleic acid binding dyes are used, a melting curve analysis is usually performed for confirmation of the presence of the amplification product.

It is understood that the present invention is not limited by the configuration of one or more commercially available instruments.

Articles of Manufacture

The invention further provides for articles of manufacture to detect vancomycin-resistant *enterococci*. An article of manufacture according to the present invention can include primers and probes used to detect nucleic acids from vancomycin-resistant *enterococci*, together with suitable packaging material. Representative primers and probes provided in a kit for detection of vancomycin-resistant *Enterococcus* can be complementary to vanA, vanB, and/or vanB-2/3 nucleic acid molecules. Methods of designing primers and probes are disclosed herein, and representative examples of primers and probes that amplify and hybridize to vanA, vanB, and/or vanB-2/3 nucleic acid molecules are provided.

Articles of manufacture of the invention also can include one or more fluorescent moieties for labeling the probes or, alternatively, the probes supplied with the kit can be labeled. For example, an article of manufacture of the invention may further include a donor fluorescent moiety for labeling one of the vanA, vanB, and/or vanB-2/3 probes and a corresponding acceptor fluorescent moiety for labeling the other vanA, vanB, and/or vanB-2/3 probe, respectively. Examples of suitable FRET donor fluorescent moieties and corresponding acceptor fluorescent moieties are provided herein.

Articles of manufacture of the invention also can contain a package insert having instructions thereon for using pairs of vanA, vanB, and/or vanB-2/3 primers and vanA, vanB, and/or vanB-2/3 probes to detect vancomycin-resistant *Enterococcus* in a biological sample. Articles of manufacture additionally may include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Sample Preparation

One hundred clinical isolates of *Enterococcus* (*E. casseliflavus/flavescens* [n=10], *E. faecalis* [n=34], *E. faecium* [n=43], *E. avium* [n=1], *E. gallinarum* [n=11], and *E. raffinosus* [n=1]) were grown on blood agar plates and evaluated for the presence of vanA, vanB, and vanB 2/3 genes using a rapid LIGHTCYCLER™ vancomycin-resistant *enteroccoci* assay. The LIGHTCYCLER™ vancomycin-resistant *enteroccoci* assay differentiates the three van genes based on the temperature range over which hybridization probes melt from the target DNA (e.g., as determined by a melting curve). Results generated using the LIGHTCYCLER™ vancomycin-resistant *enteroccoci* assay were compared to those obtained using a multiplex PCR-RFLP assay (Patel et al., 1997, *J. Clin. Microbiol.*, 35:703) and agar dilution antimicrobial susceptibility testing following the current guidelines of the National Committee for Clinical Laboratory Standards (NCCLS Document M7-A3, 1993. 57 of the 100 isolates were negative for van genes and 43 were positive (11 vanA; 11 vanB; 21 vanB-2/3) by the LIGHTCYCLER™ vancomycin-resistant *enteroccoci* assay and the PCR-RFLP assay (11 vanA; 32 vanB). The MIC values for the vanA, vanB, and vanB-2/3 positive isolates were all resistant to vancomycin at $\geq 64$ µg/ml. The MIC values for all of the other isolates were susceptible to vancomycin at $\leq 8$ µg/ml.

For each specimen culture, a 2.0 ml screw-capped tube was labeled, and 300 µl of water was pipetted into each tube. Three to five colonies from the plate were pulled with a sterile loop and placed into water. The tube was vortexed to mix. The tube was placed at 100° C. for 10 min and centrifuged at 1000×g for 1 min.

Four hundred ninety seven anal swabs collected from hospitalized patients were evaluated for the presence of vanA, vanB and vanB-2/3 genes by the LIGHTCYCLER™ vancomycin-resistant *enterococci* assay and by conventional culture methods. 482 of the 497 specimens were negative for the van genes and 12 were positive (9 vanA; 0 vanB; 3 vanB-2/3) by the LIGHTCYCLER™ vancomycin-resistant *enterococci* assay and the conventional culture screen using an 8 µg/ml *Enterococcosel* plate. The MIC values for the vanA and vanB positive isolates were all resistant to vancomycin at $\geq 64$ µg/ml. The MIC values for all of the other isolates were susceptible to vancomycin at $\leq 8$ µg/ml. An additional 21 specimens (4 vanA; 5 vanB; 12 vanB-2/3) were positive by the LIGHTCYCLER™ vancomycin-resistant *enterococci* assay but were negative by culture. Three of these patient specimens were culture positive with a repeat swab collection. Six of the positive specimens were separate specimens from the same patients. Due to the large number of vanB genotypes missed by culture and picked up with the LIGHTCYCLER™ vancomycin-resistant *enterococci* assay, the concentration of vancomycin in the *Enterococcesel* plates was decreased to 6 μg/ml, which is the usual laboratory standard (Manual of Clinical Microbiology, 7$^{th}$ Ed., 1999).

For each patient specimen obtained from an anal or stool swab, a 2.0 ml screw-capped tube was labeled with an accession label. 300 μl of water was pipetted into each tube. 1 vial of 0.1 mm zirconium beads (Daigger & Co., Inc.) was added to each tube. The swab was rinsed in the water and beads. Any liquid remaining in the swab was expressed against the side of the tube. The tubes were placed into the FastPrep apparatus and processed at a speed of 6.0 for 30 sec. Tubes were then centrifuged in a bench top centrifuge at 20,800×g for 1 min.

For nucleic acid extraction from an anal or stool specimen, 100 μl STAR buffer ( ) was added to 100 μl of each vancomycin-resistant *Enterococcal* specimen. Nucleic acid was then extracted using MagNA Pure Extraction System (Roche applied Sciences), High Pure PCR Template Preparation kit (Roche Applied Sciences, or QIAamp DNA Stool Kit (Qiagen, Inc). Positive and negative controls in STAR buffer (0.2 M citrate, 0.2 M EDTA, 0.5% ammonium lauryl sulfate, pH 5.0) were included with each nucleic acid extraction.

Example 2

Primers and Probes

Primers and probes directed toward vanA, vanB, and vanB2/3 were designed (Table 3). The vanA amplification product was 232 bp in length, the vanB amplification product was 167 bp in length, and the vanB-2/3 amplification product was 166 bp in length.

TABLE 3

Sequences of vanA, vanB, and vanB-2/3 primers and probes

| Primers | vanA | 5'-CGA GGA CGG ATA CAG GA-3' | 1 |
| | | 5'-CTT ATC ACC CCT TTA ACG C-3' | 2 |
| | vanB/ vanB-2/3 | 5'-GAA GAT ACC GTG GCT CA-3' | 5 |
| | | 5'-GTA CGG AAG AAC TTA ACG CT-3' | 6 |

| | | | SEQ ID NO: |
|---|---|---|---|
| Probes | vanA | 5'-CAA GAT AAC GGC CGC ATT GTA CTG AAC GA-3' | 3 |
| | | 5'-GTC AAT ACT CTG CCC GGT TTC AC-3' | 4 |
| | vanB/ vanB-2/3 | 5'-GAT CCA CTT CGC CGA CAA-3' | 7 |
| | | 5'-AAA TCA TCC TCG TTT CCC AT-3' | 8 | vanA, and vanB/vanB-2/3 primers were synthesized by the Mayo Core Facility on a 0.2 nm scale, and were quantitated by UV absorption at 260 nm and mixed together to make a solution containing 25 μM of each primer.

Probes were synthesized by TIB Molbiol LLC (Adelphia, N.J.), and were dissolved in TE' (10 mM Tris (pH 8.0), 0.1 mM EDTA) to a final concentration of 20 μM (resuspended according to manufacturer's instructions). The concentration of oligonucleotides and dye was double-checked by UV absorption using the following equations (*Biochemica* 1:5–8, 1999):

$$[dye] = \frac{A_{dye}}{E_{dye}} \quad [oligo] = \frac{A_{260} - \left(A_{260} \times \frac{E_{260(dye)}}{E_{dye}}\right)}{\frac{10^6}{nmol/A_{260}}}$$

Example 3

Detection Assays

For LIGHTCYCLER™ amplification to detect vancomycin-resistant *enterococci* in a stool sample, the following protocol was followed. The LIGHTCYCLER™ vancomycin-resistant *enterococci* master mix (Table 4a) was thawed, vortexed briefly, and centrifuged for 30 sec at 20,800×g. The time reagents were left at room temperature was minimized. The LIGHTCYCLER™ carousel was loaded with one cuvette per sample, two cuvettes for positive controls and the appropriate number of cuvettes for negative controls to total 5–10% of the total number of samples. 15 μl of the LIGHTCYCLER™ vancomycin-resistant *enterococci* Master Mix was added to each cuvette. 5 μl of the extracted nucleic acid was added to each LIGHTCYCLER™ cuvette.

The LIGHTCYCLER™ vancomycin-resistant *enterococci* FastStart Master Mix (Table 4b) using LIGHTCYCLER™ FastStart DNA Hybridization probe kit was also tested and results were comparable to the Master Mix having the components shown in Table 4a. The addition of a recovery template in the FastStart Master Mix was used to prevent misinterpretation of false negative results caused by inhibition of amplification. The recovery template used was a synthetic double-stranded DNA molecule with primer binding sites identical to the vanB target sequence and a unique probe binding region that allowed differentiation of recovery template from the target specific amplicon. The recovery template probes were labeled with a LC705 dye which was read in channel F3.

Table 4a. LIGHTCYCLER™ vancomycin-resistant *enterococci* Master Mix

TABLE 4a

| LightCycler ™ vancomycin-resistant enterococci Master Mix | | | |
|---|---|---|---|
| Ingredient | Stock | Mix | μl |
| Water | | | 967 |
| MgCl$_2$ | 50 mM | 2 mM | 80 |
| 10X Buffer | 10X | 1X | 200 |
| Primers-vanA | 25 μM | 0.5 μM | 40 |
| Primers-vanB | 25 μM | 0.7 μM | 56 |
| Platinum Taq | 5 U/μl | 0.03 U/μl | 12 |
| dNTP plus | 10 mM | 0.2 mM | 40 |
| BSA | 2% | 0.025% | 25 |
| Probe-vanA-FL | 20 μM | 0.2 μM | 20 |

TABLE 4a-continued

LightCycler™ vancomycin-resistant enterococci Master Mix

| Ingredient | Stock | Mix | µl |
|---|---|---|---|
| Probe-vanA-R640 | 20 µM | 0.2 µM | 20 |
| Probe-vanB/vanB-2/3-FL | 20 µM | 0.2 µM | 20 |
| Probe-vanB/vanB-2/3-R640 | 20 µM | 0.2 µM | 20 |
| Total volume -> | | | 1500 |

Table 4b. LIGHTCYCLER™ vancomycin-resistant enterococci FastStart Master Mix

TABLE 4b

LightCycler™ vancomycin-resistant enterococci FastStart Master Mix

| {LYNNE?} Ingredient | Stock | Mix | µl |
|---|---|---|---|
| Water | | | 707.3 |
| MgCl$_2$ | 25 mM | 2.5 mM | 200.0 |
| FAS 1 Reaction Mix* | 10X | 1X | 200.0 |
| Recovery Template | 10X | 1X | 200.0 |
| Primers-vanA | 25 µM | 0.5 µM | 40.0 |
| Primers-vanB | 25 µM | 0.7 µM | 56.0 |
| RT Probes-FL/Red | 24 µM | 0.2 µM | 16.7 |
| Probe-vanA-FL | 20 µM | 0.2 µM | 20.0 |
| Probe-vanA-R640 | 20 µM | 0.2 µM | 20.0 |
| Probe-vanB/vanB-2/3-FL | 20 µM | 0.2 µM | 20.0 |
| Probe-vanB/vanB-2/3-R640 | 20 µM | 0.2 µM | 20.0 |
| total volume -> | | | 1500 |

*FAS reaction mix contains 1 mM MgCl$_2$

The carousel containing the samples were centrifuged in the LIGHTCYCLER™ carousel centrifuge. The carousel was placed in the LIGHTCYCLER™ and the LIGHTCYCLER™ vancomycin-resistance enterococci program using the Master Mix shown in Table 4a was run (Table 5a). Table 5b shows the run profile used with the FastStart Master Mix. The cycling steps were complete in approximately one hour. After completion of the cycling, cuvettes were removed from the carousel with the cuvette extractor. The carousel was decontaminated in 10% bleach for 10 min, rinsed well with de-ionized water, and dried.

Table 5a. PCT cycling conditions for the LIGHTCYCLER™ vancomycin-resistant enterococci assay with the Table 4a Master Mix

TABLE 5a

PCR cycling conditions for the LightCycler™ vancomycin-resistant enterococci assay with the Table 4a Master Mix

| Program Name/Analysis mode | Analysis mode | Cycles | Temp (° C.) | Time (sec) | Temp Transition Rate (° C./sec) | Signal Acquisition |
|---|---|---|---|---|---|---|
| Initial | None | 1 | 95 | 120 | 20 | None |
| PCR | Quant. | 40 | 95 | 0 | 20 | None |
| | | | 55 | 12 | 20 | Single |
| | | | 72 | 12 | 20 | None |
| Melt Analysis | Melt | 1 | 95 | 0 | 20 | None |
| | | | 45 | 60 | 20 | None |
| | | | 80 | 0 | 0.2 | Continuous |
| Cool | None | 1 | 35 | 0 | 20 | None |

The gains were set at 1, 5, and 15 for channels F1, F2, and F3, respectively.

Table 5b. PCT cycling conditions for the LIGHTCYCLER™ vancomycin-resistant enterococci assay with FastStart Master Mix

TABLE 5b

PCR cycling conditions for the LightCycler™ vancomycin-resistant enterococci assay with FastStart Master Mix

| Program Name/Analysis mode | Analysis mode | Cycles | Temp (° C.) | Time (sec) | Temp Transition Rate (° C./sec) | Signal Acquisition |
|---|---|---|---|---|---|---|
| Initial | None | 1 | 95 | 600 | 20 | None |
| PCR | Quant. | 45 | 95 | 10 | 20 | None |
| | | | 55 | 10 | 20 | Single |
| | | | 72 | 12 | 20 | None |
| Melt Analysis | Melt | 1 | 95 | 0 | 20 | None |
| | | | 59 | 20 | 20 | None |
| | | | 45 | 20 | 0.2 | None |
| | | | 80 | 0 | 0.2 | Continuous |
| Cool | None | 1 | 40 | 30 | 20 | None |

The gains were set at 1, 5, and 30 for channels F1, F2, and F3, respectively.

The data was analyzed using the LIGHTCYCLER™ Software. A PCR melting analysis was used to differentiate vanA, vanB, and vanB-2/3 based on the Tm of the FRET probes. The probes targeting the vanA gene melt at 67±2.5° C., while the probes targeting the vanB and the vanB-2/3 gene melt at 60±2.0, and 56±2.0° C., respectfully.

A sample with a melting peak at the same location as the positive control was interpreted as positive. Positive samples were reported as positive for the presence of one or morevancomycin-resistant enterococci target sequences. A sample in which the melting curve was not above baseline was negative for the presence of vancomycin-resistant enterococci DNA. A negative result does not necessarily negate the presence of the organism or active disease.

Example 4

Results, Assay Validation, and Quality Control

Control experiments were performed to determine if the primers and probes described herein for detecting vancomycin-resistant enterococci cross-reacted with DNA from similar organisms or from organisms commonly found in the specimens. For the crossreactivity panels, the presence of microorganism DNA was initially confirmed by amplification of 16S rRNA and electrophoretic separation of the amplification product (Johnson, 1994, *Methods for General and Molecular Bacteriology*, American Society for Microbiology, Washington D.C.).

| | Stool Specificity Panel | | |
|---|---|---|---|
| ID# | Organism | Source | LC VRE |
| SP1 | *Bacteroides fragilis* | ATCC25285 | negative |
| SP2 | *Fusobacterium nucleatum* | ATCC25559 | negative |
| SP3 | *Clostridium perfringens* | ATCC13124 | negative |
| SP4 | *Bacteroides distasonis* | ATCC8503 | negative |

-continued

| ID# | Organism | Source | LC VRE |
|---|---|---|---|
| SP5 | Eubacterium lentum | ATCC43055 | negative |
| SP6 | Bacteroides thetaiotaomicrons | ATCC29741 | negative |
| SP7 | Bacteroides vulgatus | ATCC29327 | negative |
| SP8 | Echerichia vulneris | Lab Isolate | negative |
| SP9 | Klebsiella pneumoniae | ATCC700603 | negative |
| SP10 | Streptococcus viridans | QC Strain | negative |
| SP11 | Escherichia hermanii | Lab Isolate | negative |
| SP12 | Actinomyces pyogenes | Lab Isolate | negative |
| SP13 | Proteus mirabilis | QC Strain | negative |
| SP14 | Pleisomonas shigelloides | Lab Isolate | negative |
| SP15 | Salmonella Group B | CAP-D-1-69 | negative |
| SP16 | Pseudomonas aeruginosa | ATCC27853 | negative |
| SP17 | Escherichia coli | ATCC25922 | negative |
| SP18 | Aeromonas hydrophila | CAP-D-1-82 | negative |
| SP19 | Staphylococcus aureus | ATCC25923 | negative |
| SP20 | Yersinia enterocolitica | Lab Isolate | negative |
| SP21 | Staphylococcus epidermidis | MK214 | negative |
| SP22 | Shigella flexnerii | Lab Isolate | negative |
| SP23 | Citrobacter freundii | Lab Isolate | negative |
| SP24 | Salmonella species | Lab Isolate | negative |
| SP31 | Encephalitozoon intestinalis | CDC: V297 | negative |
| SP32 | Escherichia coli O157:H7 | ATCC35150 | negative |
| SP33 | Shigella dysenteriae | CDC 82-002-72 | negative |
| SP34 | Shigella sonnei | ATCC25931 | negative |
| SP35 | Escherichia coli O142:K86(B):H6 | ATCC23985 | negative |
| SP36 | Escherichia coli O70:K:H42 | ATCC23533 | negative |
| SP37 | Escherichia coli O7:K1(L):NM | ATCC23503 | negative |
| SP38 | Enterobacter cloacae | ATCC13047 | negative |

Panel of Isolates from Stool that are Vancomycin Resistant

| ID# | Organism | Source | LC VRE |
|---|---|---|---|
| SP25 | Streptococcus bovis | CAP-D-16-83 | negative |
| SP26 | Pediococcus species | Lab Isolate | negative |
| SP27 | Lactobacillus species | QC Strain | negative |
| SP28 | Leuconostoc species | Lab Isolate | negative |
| SP29 | Streptococcus bovis | Lab Isolate | negative |
| SP30 | Lactobacillus species | Lab Isolate | negative |
| SP39 | Streptococcus bovis | Lab Isolate | negative |
| SP40 | Streptococcus bovis | Lab Isolate | negative |
| SP41 | Leuconostoc species | Lab Isolate | negative |
| SP42 | Pediococcus species | Lab Isolate | negative |
| SP43 | Leuconostoc species | Lab Isolate | negative |
| SP44 | Lactobacillus species | Lab Isolate | negative |
| SP45 | Lactobacillus species | Lab Isolate | negative |
| SP46 | Leuconostoc species | Lab Isolate | negative |
| SP47 | Streptococcus bovis | Lab Isolate | negative |
| SP48 | Streptococcus bovis | Lab Isolate | negative |

Enterococcus Specificity Panel

| ID# | Organism | Source | RFLP Result | LightCycler™ |
|---|---|---|---|---|
| E1 | Enterococcus gallinarum | Lab Isolate | vanC-1 | negative |
| E2 | Enterococcus casseliflavus | Lab Isolate | vanC-2/3 | negative |
| E3 | Enterococcus faecalis | Lab Isolate | negative | negative |
| E4 | Enterococcus gallinarum | Lab Isolate | vanC-1 | negative |
| E5 | Enterococcus gallinarum | Lab Isolate | vanA and C-1 | negative |
| E6 | Enterococcus faecium | Lab Isolate | negative | negative |
| E7 | Enterococcus gallinarum | Lab Isolate | vanC-1 | negative |
| E8 | Enterococcus gallinarum | Lab Isolate | vanC-1 | negative |
| E9 | Enterococcus rhaffinosus | Lab Isolate | negative | negative |
| E10 | Enterococcus casseliflavus | Lab Isolate | vanC-2/3 | negative |
| E11 | Enterococcus gallinarum | Lab Isolate | vanC-1 | negative |
| E12 | Enterococcus faecalis | Lab Isolate | negative | negative |
| E13 | Enterococcus casseliflavus | Lab Isolate | negative | negative |
| E14 | Enterococcus faecium | Lab Isolate | negative | negative |
| E15 | Enterococcus faecalis | Lab Isolate | negative | negative |
| E16 | Enterococcus faecium | Lab Isolate | vanC-1 | negative |
| E17 | Enterococcus gallinarum | Lab Isolate | vanC-1 | negative |
| E18 | Enterococcus casseliflavus | Lab Isolate | vanC-2/3 | negative |
| E19 | Enterococcus casseliflavus | Lab Isolate | vanC-2/3 | negative |

The vanA, vanB, or vanB-2/3 primers and probes described herein did not cross-react with any of the above-indicated *Enterococcus* spp. or stool isolates tested.

In addition, control experiments were performed to determine if LIGHTCYCLER™ amplification from clinical samples produced a single amplification product. Amplification products were analyzed by 2% agarose gel electrophoresis. In positive clinical specimens, amplification using the LIGHTCYCLER™ protocol generated a single band at the expected size.

Additional control experiments were performed using dilutions of positive control plasmid to determine the sensitivity of the LIGHTCYCLER™ assay. Plasmid dilutions ranged from 0.2/µl up to $2.0 \times 10^5$/µl. Reactions were performed as described above. Data was plotted as the level of fluorescence detected relative to the cycle number for each dilution value. The slope of the standard curve was −3.236 with an r value=−1.00. Using the formulas Exponential Amplification=$10^{(-1/slope)}$, and Efficiency=$(10^{(-1/slope)})-1$, the efficiency of the reaction was determined to be 1.037152. The sensitivity of the LIGHTCYCLER™ reaction was less than 50 copies of target per 5 µl of sample with the PCR mix.

Further control experiments were performed to determine the sensitivity and specificity of the LIGHTCYCLER™ assay compared to a PCR-RFLP (restriction fragment length polymorphism) method. 60 clinical isolates of *enterococci* previously examined for the presence of a vancomycin-resistance gene by PCR-RFLP were instant gene by PCR-RFLP were tested using the LIGHTCYCLER™ assay described herein. The isolates were grown on blood agar plates at 37° C. overnight. Cells from *enterococci* colonies were lysed by suspending the colony in 500 µl sterile water and boiling the sample at 100° C. for 10 minutes. The tube then was centrifuged for 1 minute at 20,800×g, and 5 µl of the supernatant was analyzed by the LIGHTCYCLER™ assay described herein.

The LIGHTCYCLER™ assay described herein correlated 100% with the results from the PCR-RFLP assay (27 samples were positive for vancomycin-resistant *enterococci*; 33 samples were negative for vancomycin-resistant *enterococci*). Note that vanC genotypes are detected with the PCR-RFLP assay, although the current LIGHTCYCLER™ assay does not detect genotypes that are negative for the vancomycin-resistance phenotype.

| # | PCR-RFLP | LightCycler™ | Organism |
|---|---|---|---|
| 1 | vanA | vanA | E. faecium |
| 2 | vanA | vanA | E. faecium |
| 4 | vanA | vanA | E. faecium |
| 5 | vanB | vanB | E. faecium |
| 6 | negative | negative | E. faecalis |
| 7 | negative | negative | E. faecalis |
| 9 | negative | negative | E. faecalis |
| 10 | vanB | vanB-2/3 | E. faecium |
| 11 | vanA | vanA | E. faecium |
| 13 | vanA | vanA | E. faecium |
| 15 | vanB | vanB-2/3 | E. faecium |
| 16 | vanB | vanB | E. faecium |
| 17 | vanB | vanB | E. faecium |
| 19 | negative | negative | E. faecalis |
| 20 | negative | negative | E. faecalis |
| 21 | vanC-2/3 | negative | E. casseliflavus |
| 23 | negative | negative | E. avium |
| 25 | negative | negative | E. faecalis |
| 28 | vanB | vanB | E. faecium |
| 29 | negative | negative | E. faecalis |
| 30 | negative | negative | E. faecalis |
| 31 | vanB | vanB | E. faecium |
| 32 | vanC-2/3 | negative | E. casseliflavus |
| 33 | vanB | vanB-2/3 | E. faecium |
| 34 | vanB | vanB-2/3 | E. faecium |
| 35 | vanB | vanB | E. faecalis |
| 36 | negative | negative | E. faecium |
| 38 | vanB | vanB-2/3 | E. faecium |
| 39 | negative | negative | E. faecalis |
| 40 | negative | negative | E. faecalis |
| 41 | vanC | negative | E. faecalis |
| 42 | vanC-1 | negative | E. gallinarum |
| 44 | vanC-2/3 | negative | E. casseliflavus |
| 45 | vanB | vanB-2/3 | E. faecalis |
| 46 | vanB | vanB-2/3 | E. faecium |
| 47 | vanB | vanB-2/3 | E. faecium |
| 48 | negative | negative | E. faecalis |
| 49 | negative | negative | E. faecalis |
| 50 | negative | negative | E. faecalis |
| 51 | vanB | vanB | E. faecium |
| 54 | vanB | vanB-2/3 | E. faecium |
| 55 | vanB | vanB-2/3 | E. faecium |
| 56 | vanB | vanB | E. faecalis |
| 57 | negative | negative | E. faecalis |
| 58 | negative | negative | E. faecium |
| 59 | negative | negative | E. faecalis |
| 60 | negative | negative | E. faecalis |
| 61 | vanA | vanA | E. faecium |
| 62 | vanB-v | vanB-2/3 | E. faecium |
| 63 | vanA | vanA | E. faecium |
| 64 | negative | negative | E. faecalis |
| 65 | negative | negative | E. casseliflavus |
| 66 | vanC-1 | negative | E. gallinarum |
| 67 | vanB | vanB-2/3 | E. faecium |
| 68 | vanC-1 | negative | E. gallinarum |
| 69 | negative | negative | E. faecalis |
| 70 | negative | negative | E. faecalis |
| 71 | negative | negative | E. faecalis |
| 72 | vanC-2/3 | negative | E. casseliflavus |
| 74 | negative | negative | E. faecium |

An additional 56 specimens obtained from anal swabs were analyzed using the LIGHTCYCLER™ assay and were compared to a culture method using a VRE screen media. The anal swabs were prepared for amplification as described above. The LIGHTCYCLER™ assay detected more positive specimens than did culture, and is therefore more sensitive than culture. A high rate of false negative results from rectal swab culture has been previously confirmed in the literature (*Clin. Infect. Dis.*, 2002, 34:167–172).

|  |  | Culture (Gold Standard) | | |
|---|---|---|---|---|
|  |  | VRE Positive | VRE Negative | TOTAL |
| LightCycler™ VRE Assay | VRE Positive | 7 | 5 | 12 |
|  | VRE Negative | 0 | 44 | 44 |
|  | TOTAL | 7 | 49 | 56 |

| # | Culture Results[a] | Susceptibility Results[b] | LightCycler™ Results |
|---|---|---|---|
| 52 | Enterococcus | Amp, Pen, Gent = S; Van = I | VanA |
| 129 | NG |  | VanB |
| 235 | Enterococcus | Amp, Van, Pen, Gent = R | VanA |
| 244 | Enterococcus | Amp, Van, Pen = R; Gent = S | VanA |
| 279 | Enterococcus | Amp, Pen = R; Van, Gent = S | VanB-2/3 |
| 280 | NG |  | Negative |
| 281 | NG |  | Negative |
| 282 | NG |  | Negative |
| 286 | Enterococcus | Amp, Van, Pen, Gent = S | VanB-2/3 (weak) |
| 287 | NG |  | Negative |
| 296 | Enterococcus | Amp, Van, Pen, Gent = S | Negative |
| 298 | NG |  | Negative |
| 299 | NG |  | Negative |
| 300 | NG |  | Negative |
| 301 | NG |  | Negative |
| 302 | NG |  | Negative |
| 303 | NG |  | Negative |
| 304 | Enterococcus | Amp, Pen, Gent = S; Van = I | Negative |
| 305 | NG |  | Negative |
| 306 | NG |  | Negative |
| 307 | NG |  | VanB-2/3 |
| 308 | NG |  | Negative |
| 309 | NG |  | Negative |
| 310 | NG | Follow-up specimen positive | VanB-2/3 |
| 311 | NG |  | Negative |
| 319 | NG |  | Negative |
| 338 | NG |  | Negative |
| 348 | NG |  | Negative |
| 419 | Enterococcus | Amp, Van, Pen = R; Gent = I | VanA |
| 420 | NG |  | Negative |
| 421 | NG |  | Negative |
| 422 | NG |  | Negative |
| 423 | NG |  | Negative |
| 424 | NG |  | Negative |
| 425 | Enterococcus | Amp, Pen, Gent = S; Van = I | Negative |
| 426 | NG |  | Negative |
| 448 | NG |  | Negative |
| 449 | NG |  | VanB-2/3 (weak) |
| 450 | NG |  | Negative |
| 451 | NG |  | Negative |
| 452 | NG |  | Negative |
| 453 | NG |  | VanB |
| 454 | NG |  | Negative |
| 455 | NG |  | Negative |
| 469 | NG |  | Negative |
| 470 | NG |  | Negative |
| 471 | NG |  | Negative |
| 472 | NG |  | Negative |
| 473 | NG |  | VanB-2/3 |
| 474 | NG |  | Negative |
| 475 | NG |  | Negative |
| 476 | NG |  | Negative |
| 525 | NG |  | Negative |
| 526 | NG |  | Negative |
| 527 | NG |  | VanB-2/3 |
| 528 | NG |  | Negative |

[a]NG, No growth.
[b]Amp, Ampicillan; Pen, Pennicillin; Gent, Gentamycin; Van, Vancomycin.
[b]R, Resistant; S, Susceptible; I, Intermediate.

Control experiments also were performed to determine the precision (e.g., within-run, within-day, and between-day precision) of the LIGHTCYCLER™ assay. Within-run precision of the LIGHTCYCLER™ assay was evaluated by assaying 5 µl of a positive control dilution 20 times within the same amplification experiment. Within-day precision of the LIGHTCYCLER™ assay was evaluated by assaying 5 µl of a positive control dilution 20 times during a single day. Between-day precision of the LIGHTCYCLER™ assay was evaluated by assaying 5 µl of positive control dilution 20 times over a three-day period.

The average number of cycles at which FRET was detected in the within-run assays was 30.82±0.293; the average number of cycles at which FRET was detected in the within-day assays was 30.61±0.190; and the average number of cycles at which FRET was detected in the between-day precision was 30.61±0.190 (day1), 30.17±0.154 (day2), and 29.41±0.143 (day3). The precision of the average crossing point measurement and the standard deviation of the 20 points was excellent.

Control experiments were performed to determine if the LightCycler™ assay produces the same results using 2, 5 or 10 µl of the nucleic acid sample extracted from a patient's sample. Mixes were prepared for different target volumes essentially as described above, and a set of 2 positive samples (vanA and vanB-2/3) was tested at each volume. Similar results were obtained from patient specimens when 5 or 10 µl of sample was used in the assay. The cross points were within one cycle. A difference of 2–3 cycles was observed when 2 µl of sample was used.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said pair of vanA primers comprises a first vanA primer and a second vanA primer, wherein said first vanA primer is no more than 30 nucleotides in length and comprises the sequence 5'-CGA GGA CGG ATA CAG GA-3' (SEQ ID NO:1), wherein said hybridizing step comprises contacting said sample with a pair of vanA probes, wherein the members of said pair of vanA probes hybridize to said amplification product within no more than five nucleotides of each other, wherein a first vanA probe of said pair of vanA probes is labeled with a donor fluorescent moiety and wherein a second vanA probe of said pair of vanA probes is labeled with a corresponding acceptor fluorescent moiety; and detecting the presence or absence of fluorescence resonance energy transfer (FRET) between said donor fluorescent moiety of said first vanA probe and said acceptor fluorescent moiety of said second vanA probe, wherein the presence of FRET is indicative of the presence of vancomycin-resistant *enterococci* in said biological sample, and wherein the absence of FRET is indicative of the absence of vancomycin-resistant *enterococci* in said biological sample.

2. The method of claim 1, wherein said second vanA primer comprises the sequence 5'-CTT ATC ACC CCT TTAACG C-3' (SEQ ID NO:2).

3. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said pair of vanA primers comprises a first vanA primer and a second vanA primer, wherein said second vanA primer is no more than 30 nucleotides in length and comprises the sequence 5'-CTT ATC ACC CCT TTA ACG C-3' (SEQ ID NO:2), wherein said hybridizing step comprises contacting said sample with a pair of vanA probes, wherein the members of said pair of vanA probes hybridize to said amplification product within no more than five nucleotides of each other, wherein a first vanA probe of said pair of vanA probes is labeled with a donor fluorescent moiety and wherein a second vanA probe of said pair of vanA probes is labeled with a corresponding acceptor fluorescent moiety; and detecting the presence or absence of fluorescence resonance energy transfer (FRET) between said donor fluorescent moiety of said first vanA probe and said acceptor fluorescent moiety of said second vanA probe, wherein the presence of FRET is indicative of the presence of vancomycin-resistant *enterococci* in said biological sample, and wherein the absence of FRET is indicative of the absence of vancomycin-resistant *enterococci* in said biological sample.

4. The method of claim 3, wherein said first vanA primer comprises the sequence 5'-CGA GGA CGG ATA CAG GA-3' (SEQ ID NO:1).

5. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said hybridizing step comprises contacting said sample with a pair of vanA probes, wherein the members of said pair of vanA probes hybridize to said amplification product within no more than five nucleotides of each other, wherein a first vanA probe of said pair of vanA probes is labeled with a donor fluorescent moiety and wherein a second vanA probe of said pair of vanA probes is labeled with a corresponding acceptor fluorescent moiety, wherein said first vanA probe is no more than 30 nucleotides in length and comprises the sequence 5'-CAA GAT AAC GGC CGC ATT GTA CTG AAC GA-3' (SEQ ID NO:3); and detecting the presence or absence of fluorescence resonance energy transfer (FRET) between said donor fluorescent moiety of said first vanA probe and said acceptor fluorescent moiety of said second vanA probe, wherein the presence of FRET is indicative of the presence of vancomycin-resistant *enterococci* in said biological sample, and wherein the absence of FRET is indicative of the absence of vancomycin-resistant *enterococci* in said biological sample.

6. The method of claim 5, wherein said second vanA probe comprises the sequence 5'-GTC AAT ACT CTG CCC GGT TTC AC-3' (SEQ ID NO:4).

7. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said hybridizing step comprises contacting said sample with a pair of vanA probes, wherein the members of said pair of vanA probes hybridize to said amplification product within no more than five nucleotides of each other, wherein a first vanA probe of said pair of vanA probes is labeled with a donor fluorescent moiety and wherein a second vanA probe of said pair of vanA probes is labeled with a corresponding acceptor fluorescent moiety, wherein said second vanA probe is no more than 30 nucleotides in length and comprises the sequence 5'-GTC AAT ACT CTG CCC GGT TTC AC-3' (SEQ ID NO:4); and detecting the presence or absence of fluorescence resonance energy transfer (FRET) between said donor fluorescent moiety of said first vanA probe and said acceptor fluorescent moiety of said second vanA probe, wherein the presence of FRET is indicative of the presence of vancomycin-resistant *enterococci* in said biological sample, and wherein the absence of FRET is indicative of the absence of vancomycin-resistant *enterococci* in said biological sample.

8. The method of claim 7, wherein said first vanA probe comprises the sequence 5'-CAA GAT AAC GGC CGC ATT GTA CTG AAC GA-3' (SEQ ID NO:3).

9. The method of claim 1, 3, 5, or 7, wherein the presence of said FRET within 50 cycling steps is indicative of the presence of a vancomycin-resistant *enterococci* infection in said individual.

10. The method of claim 1, 3, 5, or 7, wherein the presence of said FRET within 40 cycling steps is indicative of the presence of a vancomycin-resistant *enterococci* infection in said individual.

11. The method of claim 1, 3, 5, or 7, wherein the presence of said FRET within 30 cycling steps is indicative of the presence of a vancomycin-resistant *enterococci* infection in said individual.

12. The method of claim 1, 3, 5, or 7, wherein said cycling step is performed on a control sample.

13. The method of claim 12, wherein said control sample comprises said vancomycin-resistant *enterococci* vanA nucleic acid molecule.

14. The method of claim 1, 3, 5, or 7, wherein said cycling step uses a pair of control primers and a pair of control probes, wherein said control primers and said control probes are other than said vanA primers and said vanA probes, wherein a control amplification product is produced if control template is present in said sample, wherein said control probes hybridize to said control amplification product.

15. The method of claim 1, 3, 5, or 7, further comprising:

performing at least one cycling step, wherein said cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said hybridizing step comprises contacting said sample with a pair of vanB probes, wherein the members of said pair of vanB probes hybridize within no more than five nucleotides of each other, wherein a first vanB probe of said pair of vanB probes is labeled with a donor fluorescent moiety and wherein a second vanB probe of said pair of vanB probes is labeled with a corresponding acceptor fluorescent moiety; and detecting the presence or absence of FRET between said donor fluorescent moiety of said first vanB probe and said acceptor fluorescent moiety of said second vanB probe upon hybridization of said pair of vanB probes to said targets.

16. The method of claim 15, wherein said pair of vanB primers comprises a first vanB primer and a second vanB primer, wherein said first vanB primer comprises the sequence 5'-GAA GAT ACC GTG GCT CA-3' (SEQ ID NO:5), and wherein said second vanB primer comprises the sequence 5'-GTA CGG AAG AAC TTA ACG CT-3' (SEQ ID NO:6).

17. The method of claim 15, wherein said first vanB probe comprises the sequence 5'-GAT CCA CTT CGC CGA CAA-3' (SEQ ID NO:7), and wherein said second vanB probe comprises the sequence 5'-AAA TCA TCC TCG TTT CCC AT- 3' (SEQ ID NO:8).

18. A method for detecting the presence or absence of vancomycin-resistant *enterococci* in a biological sample from an individual, said method comprising:
   performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said pair of vanB primers comprises a first vanB primer and a second vanB primer, wherein said first vanB primer is no more than 30 nucleotides in length and comprises the sequence 5'-GAA GAT ACC GTG GCT CA-3' (SEQ ID NO:5), wherein said hybridizing step comprises contacting said sample with a pair of vanB probes, wherein the members of said pair of vanB probes hybridize within no more than five nucleotides of each other, wherein a first vanB probe of said pair of vanB probes is labeled with a donor fluorescent moiety and wherein a second vanB probe of said pair of vanB probes is labeled with a corresponding acceptor fluorescent moiety; and
   detecting the presence or absence of fluorescence resonance energy transfer (FRET) between said donor fluorescent moiety of said first vanB probe and said acceptor fluorescent moiety of said second vanB probe upon hybridization of said pair of vanB probes to said targets,
   wherein the presence of FRET is indicative of the presence of vancomycin-resistant *enterococci* in said biological sample, and wherein the absence of FRET is indicative of the absence of vancomycin-resistant *enterococci* in said biological sample.

19. The method of claim 18, wherein said second vanB primer comprises the sequence 5'-GTA CGG AAG AAC TTA ACG CT-3' (SEQ ID NO:6).

20. A method for detecting the presence or absence of vancomycin-resistant *enterococci* in a biological sample from an individual, said method comprising:
   performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said pair of vanB primers comprises a first vanB primer and a second vanB primer, wherein said second vanB primer is no more than 30 nucleotides in length and comprises the sequence 5'-GTA CGG AAG AAC TTA ACG CT-3' (SEQ ID NO:6), wherein said hybridizing step comprises contacting said sample with a pair of vanB probes, wherein the members of said pair of vanB probes hybridize within no more than five nucleotides of each other, wherein a first vanB probe of said pair of vanB probes is labeled with a donor fluorescent moiety and wherein a second vanB probe of said pair of vanB probes is labeled with a corresponding acceptor fluorescent moiety; and
   detecting the presence or absence of fluorescence resonance energy transfer (FRET) between said donor fluorescent moiety of said first vanB probe and said acceptor fluorescent moiety of said second vanB probe upon hybridization of said pair of vanB probes to said targets,
   wherein the presence of FRET is indicative of the presence of vancomycin-resistant *enterococci* in said biological sample, and wherein the absence of FRET is indicative of the absence of vancomycin-resistant *enterococci* in said biological sample.

21. The method of claim 20, wherein said first vanB primer comprises the sequence 5'-GAA GAT ACC GTG GCT CA-3' (SEQ ID NO:5).

22. A method for detecting the presence or absence of vancomycin-resistant *enterococci* in a biological sample from an individual, said method comprising:
   performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said hybridizing step comprises contacting said sample with a pair of vanB probes, wherein the members of said pair of vanB probes hybridize within no more than five nucleotides of each other, wherein a first vanB probe of said pair of vanB probes is labeled with a donor fluorescent moiety and wherein a second vanB probe of said pair of vanB probes is labeled with a corresponding acceptor fluorescent moiety, wherein said first vanB probe is no more than 30 nucleotides in length and comprises the sequence 5'-GAT CCA CTT CGC CGA CAA-3' (SEQ ID NO:7); and
   detecting the presence or absence of fluorescence resonance energy transfer (FRET) between said donor fluorescent moiety of said first vanB probe and said acceptor fluorescent moiety of said second vanB probe upon hybridization of said pair of vanB probes to said targets,
   wherein the presence of FRET is indicative of the presence of vancomycin-resistant *enterococci* in said biological sample, and wherein the absence of FRET is indicative of the absence of vancomycin-resistant *enterococci* in said biological sample.

23. The method of claim 22, wherein said second vanB probe comprises the sequence 5'-AAA TCA TCC TCG TTT CCC AT-3' (SEQ ID NO:8).

24. A method for detecting the presence or absence of vancomycin-resistant *enterococci* in a biological sample from an individual, said method comprising:
   performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said hybridizing step comprises contacting said sample with a pair of vanB probes, wherein the members of said pair of vanB probes hybridize within no more than five nucleotides of each other, wherein a first vanB probe of said pair of vanB probes is labeled with a donor fluorescent moiety and wherein a second vanB probe of said pair of vanB probes is labeled with a corresponding acceptor fluorescent moiety, wherein said second vanB probe is no more than 30 nucleotides in length and comprises the sequence 5'-AAA TCA TCC TCG TTT CCC AT-3' (SEQ ID NO:8); and detecting the presence or absence of fluorescence resonance energy transfer (FRET) between said donor fluorescent moiety of said first vanB probe and said acceptor fluorescent moiety of said second vanB probe upon hybridization of said pair of vanB probes to said targets, wherein the presence of FRET is indicative of the presence of vancomycin-resistant *enterococci* in said biological sample, and wherein the absence of FRET is indicative of the absence of vancomycin-resistant *enterococci* in said biological sample.

25. The method of claim 24, wherein said first vanB probe comprises the sequence 5'-GAT CCA CTT CGC CGA CAA-3' (SEQ ID NO:7).

26. The method of claim 18, 20, 22, or 24, wherein the presence of said FRET within 50 cycling steps is indicative of the presence of a vancomycin-resistant *enterococci* infection in said individual.

27. The method of claim 18, 20, 22, or 24, wherein the presence of said FRET within 40 cycling steps is indicative of the presence of a vancomycin-resistant *enterococci* infection in said individual.

28. The method of claim 18, 20, 22, or 24, wherein the presence of said FRET within 30 cycling steps is indicative of the presence of a vancomycin-resistant *enterococci* infection in said individual.

29. The method of claim 18, 20, 22, or 24, wherein said cycling step is performed on a control sample.

30. The method of claim 29, wherein said control sample comprises said vancomycin-resistant *enterococci* vanB nucleic acid molecule.

31. The method of claim 18, 20, 22, or 24, wherein said cycling step uses a pair of control primers and a pair of control probes, wherein said control primers and said control probes are other than said vanB primers and said vanB probes, wherein a control amplification product is produced if control template is present in said sample, wherein said control probes hybridize to said control amplification product.

32. The method of claim 1, 3, 5, 7, 18, 20, 22, or 24, wherein the members of said pair of probes hybridize within no more than two nucleotides of each other.

33. The method of claim 1, 3, 5, 7, 18, 20, 22, or 24, wherein the members of said pair of probes hybridize within no more than one nucleotide of each other.

34. The method of claim 1, 3, 5, 7, 18, 20, 22, or 24, wherein said donor fluorescent moiety is fluorescein.

35. The method of claim 1, 3, 5, 7, 18, 20, 22, or 24, wherein said detecting step comprises exciting said biological sample at a wavelength absorbed by said donor fluorescent moiety and visualizing and/or measuring the wavelength emitted by said acceptor fluorescent moiety.

36. The method of claim 1, 3, 5, 7, 18, 20, 22, or 24, wherein said detecting comprises quantitating said FRET.

37. The method of claim 1, 3, 5, 7, 18, 20, 22, or 24, wherein said detecting step is performed after each cycling step.

38. The method of claim 1, 3, 5, 7, 18, 20, 22, or 24, wherein said detecting step is performed in real time.

39. The method of claim 1, 3, 5, 7, 18, 20, 22, or 24, further comprising determining the melting temperature between one or both of said probe(s) and said amplification product, wherein said melting temperature confirms said presence or said absence of said vancomycin-resistant *enterococci* or vancomycin-resistant *enterococci*.

40. The method of claim 1, 3, 5, 7, 18, 20, 22, or 24, further comprising preventing amplification of a contaminant nucleic acid.

41. The method of claim 40, wherein said preventing comprises performing said amplifying step in the presence of uracil.

42. The method of claim 41, wherein said preventing further comprises treating said biological sample with uracil-DNA glycosylase prior to a first amplification step.

43. The method of claim 1, 3, 5, 7, 18, 20, 22, or 24, wherein said biological sample is selected from the group consisting of stool samples, anal or perirectal swabs, blood, and body fluids.

44. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said pair of vanA primers comprises a first vanA primer and a second vanA primer, wherein said first vanA primer comprises the sequence 5'-CGA GGA CGG ATA CAG GA-3' (SEQ ID NO:1), wherein said hybridizing step comprises contacting said sample with a vanA probe, wherein said vanA probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said vanA probe, wherein the presence or absence of FRET is indicative of the presence or absence of vancomycin-resistant *enterococci* in said sample.

45. The method of claim 44, wherein said second vanA primer comprises the sequence 5'-CTT ATC ACC CCT TTA ACG C-3' (SEQ ID NO:2).

46. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said pair of vanA primers comprises a first vanA primer and a second vanA primer, wherein said second vanA primer comprises the sequence 5'-CTT ATC ACC CCT TTA ACG C-3' (SEQ ID NO:2), wherein said hybridizing step comprises contacting said sample with a vanA probe, wherein said vanA probe is labeled with a donor fluorescent moiety and a corresponding acceptor fluorescent moiety; and detecting the presence or absence of fluorescent resonance energy transfer (FRET) between said donor fluorescent moiety and said acceptor fluorescent moiety of said vanA probe, wherein the presence or absence of FRET is indicative of the presence or absence of vancomycin-resistant *enterococci* in said sample.

47. The method of claim 46, wherein said first vanA primer comprises the sequence 5'-CGA GGA CGG ATA CAG GA-3' (SEQ ID NO:1).

48. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanA primers to produce a vanA amplification product if a vancomycin-resistant *enterococci* vanA nucleic acid molecule is present in said sample, wherein said hybridizing step comprises contacting said sample with a vanA probe, wherein said vanA probe is labeled with a donor fluorescent moiety and a corresponding acceptor fluorescent moiety, wherein said vanA probe comprises a sequence selected from the group consisting of 5'-CAA GAT AAC GGC CGC ATT GTA CTG AAC GA-3' (SEQ ID NO:3) and 5'-GTC AAT ACT CTG CCC GGT TTC AC-3' (SEQ ID NO:4); and detecting the presence or absence of fluorescence resonance energy transfer (FRET) between said donor fluorescent moiety and said acceptor fluorescent moiety of said vanA probe, wherein the presence or absence of FRET is indicative of the presence or absence of vancomycin-resistant *enterococci* in said sample.

49. The method of claim 48, wherein said first and second vanA primers comprise the sequences 5'-CGA GGA CGG ATA CAG GA-3' (SEQ ID NO:1) and 5'-CTT ATC ACC CCT TTA ACG C-3' (SEQ ID NO:2), respectively.

50. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said pair of vanB primers comprises a first vanB primer and a second vanB primer, wherein said first vanB primer comprises the sequence 5'-GAA GAT ACC GTG GCT CA-3' (SEQ ID NO:5), wherein said hybridizing step comprises contacting said sample with a vanB probe, wherein said vanB probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said vanB probe, wherein the presence or absence of FRET is indicative of the presence or absence of vancomycin-resistant *enterococci* in said sample.

51. The method of claim 50, wherein said second vanB primer comprises the sequence 5'-GTA CGG AAG AAC TTA ACG CT-3' (SEQ ID NO:6).

52. A method for detecting the presence or absence or vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said pair of vanB primers comprises a first vanB primer and a second vanB primer, wherein said second vanB primer comprises the sequence 5'-GTA CGG AAG AAC TTA ACG CT-3' (SEQ ID NO:6), wherein said hybridizing step comprises contacting said sample with a vanB probe, wherein said vanB probe is labeled with a donor fluorescent moiety and a corresponding acceptor fluorescent moiety, and detecting the presence or absence of fluorescence resonance energy transfer (FRET) between said donor fluorescent moiety and said acceptor fluorescent moiety of said vanB probe, wherein the presence or absence of FRET is indicative of the presence or absence of vancomycin-resistant *enterococci* in said sample.

53. The method of claim 52, wherein said first vanB primer comprises the sequence 5'-GAA GAT ACC GTG GCT CA-3' (SEQ ID NO:5).

54. A method for detecting the presence or absence of vancomycin-resistant *enterococci* in a biological sample from an individual, said method comprising:

performing at least one cycling step, wherein a cycling step comprises an amplifying step and a hybridizing step, wherein said amplifying step comprises contacting said sample with a pair of vanB primers to produce a vanB amplification product if a vancomycin-resistant *enterococci* vanB nucleic acid molecule is present in said sample, wherein said hybridizing step comprises contacting said sample with a vanB probe, wherein said vanB probe is labeled with a donor fluorescent moiety and a corresponding acceptor fluorescent moiety, wherein said vanB probe comprises a sequence selected from the group consisting of 5'-GAT CCA CTT CGC CGA CAA-3' (SEQ ID NO:7) and 5'-AAA TCA TCC TCG TTT CCC AT-3' (SEQ ID NO:8); and detecting the presence or absence of fluorescence resonance energy transfer (FRET) between said donor fluorescent moiety and said acceptor fluorescent moiety of said vanB probe, wherein the presence or absence of FRET is indicative of the presence or absence of vancomycin-resistant *enterococci* in said sample.

55. The method of claim 54, wherein said first and second vanB primers comprise the sequences 5'-GAA GAT ACC GTG GCT CA-3' (SEQ ID NO:5) and 5'-GTA CGG AAG AAC TTA ACG CT-3' (SEQ ID NO:6).

56. The method of claim 44, 46, 48, 50, 52, or 54, wherein said amplification employs a polymerase enzyme having 5' to 3' exonuclease activity.

57. The method of claim 44, 46, 48, 50, 52, or 54, wherein said donor and acceptor fluorescent moieties are within no more than 5 nucleotides of each other on said probe.

58. The method of claim 57, wherein said acceptor fluorescent moiety is a quencher.

59. The method of claim 44, 46, 48, 50, 52, or 54, wherein said probe comprises a nucleic acid sequence that permits secondary structure formation, wherein said secondary structure formation results in spatial proximity between said donor and said acceptor fluorescent moiety.

60. The method of claim 59, wherein said acceptor fluorescent moiety is a quencher.

61. A method for detecting the presence or absence of vancomycin-resistant *enterococci* in a biological sample from an individual, said method comprising:

performing at least one cycling step, wherein a cycling step comprises an amplifying step and a dye-binding step, wherein said amplifying step comprises contacting said sample with a pair of vanA primers to produce a vanA amplification product if a vancomycin-resistant *enterococci* vanA nucleic acid molecule is present in said sample, wherein said pair of vanA primers comprises a first vanA primer and a second vanA primer, wherein said first vanA primer comprises the sequence 5'-CGA GGA CGG ATA GAG GA-3' (SEQ ID NO: 1), wherein said dye-binding step comprises contacting said vanA amplification product with a nucleic acid binding dye; and detecting the presence or absence of binding of said nucleic acid binding dye to said amplification product, wherein the presence of binding is indicative of the presence of vancomycin-resistant *enterococci* in said sample, and wherein the absence of binding is indicative of the absence of vancomycin-resistant *enterococci* in said sample.

62. The method of claim 61, wherein said second vanA primer comprises the sequence 5'-CTT ATC ACC CCT TTA ACG C-3' (SEQ ID NO:2).

63. A method for detecting the presence or absence of vancomycin-resistant *enterococci* in a biological sample from an individual, said method comprising:

performing at least one cycling step, wherein a cycling step comprises an amplifying step and a dye-binding step, wherein said amplifying step comprises contacting said sample with a pair of vanA primers to produce a vanA amplification product if a vancomycin-resistant *enterococci* vanA nucleic acid molecule is present in said sample, wherein said pair or vanA primers comprises a first vanA primer and a second vanA primer, wherein said second vanA primer comprises the sequence 5'-CTT ATC ACC CCT TTA ACG C-3' (SEQ ID NO:2), wherein said dye-binding step comprises contacting said vanA amplification product with a nucleic acid binding dye; and detecting the presence or absence of binding of said nucleic acid binding dye to said amplification product, wherein the presence of binding is indicative of the presence of vancomycin-resistant *enterococci* in said sample, and wherein the absence of binding is indicative of the absence of vancomycin-resistant *enterococci* in said sample.

64. The method of claim 63, wherein said first vanA primer comprises the sequence 5'-CGA GGA CGG ATA CAG GA-3' (SEQ ID NO:1).

65. A method for detecting the presence or absence of vancomycin-resistant *enterococci* in a biological sample from an individual, said method comprising:

performing at least one cycling step, wherein a cycling step comprises an amplifying step and a dye-binding step, wherein said amplifying step comprises contacting said sample with a pair of vanB primers to produce a vanB amplification product if a vancomycin-resistant *enterococci* vanB nucleic acid molecule is present in said sample, wherein said pair of vanB primers comprises a first vanB primer and a second vanB primer, wherein said first vanB primer comprises the sequence 5'-GAA GAT ACC GTG GCT CA-3' (SEQ ID NO:5), wherein said dye-binding step comprises contacting said vanB amplification product with a nucleic acid binding dye; and detecting the presence or absence of binding of said nucleic acid binding dye to said amplification product, wherein the presence of binding is indicative or the presence of vancomycin-resistant *enterococci* in said sample, and wherein the absence of binding is indicative of the absence of vancomycin-resistant *enterococci* in said sample.

66. The method of claim 65, wherein said second vanB primer comprises the sequence 5'-GTA CGG AAG AAC TTA ACG CT-3' (SEQ ID NO:6).

67. A method for detecting the presence or absence of vancomycin-resistant *enterococci* in a biological sample from an individual, said method comprising:

performing at least one cycling step, wherein a cycling step comprises an amplifying step and a dye-binding step, wherein said amplifying step comprises contacting said sample with a pair of vanB primers to produce a vanB amplification product if a vancomycin-resistant *enterococci* vanB nucleic acid molecule is present in said sample, wherein said pair of vanB primers comprises a first vanB primer and a second vanB primer, wherein said second vanB primer comprises the sequence 5'-GTA CGG AAG AAC TTA ACG CT-3' (SEQ ID NO:6), wherein said dye-binding step comprises contacting said vanB amplification product with a nucleic acid binding dye; and detecting the presence or absence of binding of said nucleic acid binding dye to said amplification product, wherein the presence of binding is indicative of the presence of vancomycin-resistant *enterococci* in said sample, and wherein the absence of binding is indicative of the absence of vancomycin-resistant *enterococci* in said sample.

68. The method of claim 67, wherein said first vanB primer comprises the sequence 5'-GAA GAT ACC GTG GCT CA-3' (SEQ ID NO:5).

69. The method of claim 61, 63, 65, or 67, wherein said nucleic acid binding dye is ethidium bromide.

70. The method of claim 61, 63, 65, or 67, further comprising determining the melting temperature between said amplification product and said nucleic acid binding dye, wherein said melting temperature confirms said presence or absence of said vancomycin-resistant *enterococci*.

* * * * *

UNITED STATES PATENT AND TRADEMARK OFFICE
CERTIFICATE OF CORRECTION

| | | |
|---|---|---|
| PATENT NO. | : 7,074,598 B2 | Page 1 of 1 |
| APPLICATION NO. | : 10/254260 | |
| DATED | : July 11, 2006 | |
| INVENTOR(S) | : Franklin R. Cockerill, III and Lynne M. Sloan | |

It is certified that error appears in the above-identified patent and that said Letters Patent is hereby corrected as shown below:

Title Page, (56) References Cited, Other Publications, 7th GenBank Accession reference, please delete "270527" and insert --Z70527--therefor;

Title Page (56) (Page 2), References Cited, Other Publications, Bélanger et al. reference, please delete "Multriplex" and insert --Multiplex--therefor;

Column 45, line 55, after "detecting" please insert --step--;

Column 47, line 57, please delete "or" and insert --of--therefor;

Column 49, line 29, please delete "or" and insert --of--therefor;

Column 50, line 11, please delete "or" and insert --of--therefor.

Signed and Sealed this

Fourteenth Day of November, 2006

JON W. DUDAS
*Director of the United States Patent and Trademark Office*